US008451328B2

(12) United States Patent
Yoshino et al.

(10) Patent No.: US 8,451,328 B2
(45) Date of Patent: May 28, 2013

(54) IMAGE PROCESSING DEVICE, IMAGING DEVICE, COMPUTER-READABLE DEVICE, AND IMAGE PROCESSING METHOD FOR PROCESSING A FLUORESCENCE IMAGE

(75) Inventors: Koichiro Yoshino, Tokyo (JP); Hiroshi Suzuki, Hachioji (JP)

(73) Assignee: Olympus Corporation, Tokyo (JP)

(*) Notice: Subject to any disclaimer, the term of this patent is extended or adjusted under 35 U.S.C. 154(b) by 416 days.

(21) Appl. No.: 12/730,289

(22) Filed: Mar. 24, 2010

(65) Prior Publication Data
US 2010/0245616 A1  Sep. 30, 2010

(30) Foreign Application Priority Data

Mar. 26, 2009  (JP) .................................. 2009-077563

(51) Int. Cl.
*A62B 1/04* (2006.01)
*H04N 5/228* (2006.01)

(52) U.S. Cl.
USPC ........................................ 348/65; 348/222.1

(58) Field of Classification Search
USPC ..................................... 348/65, 68, 72, 222.1
See application file for complete search history.

(56) References Cited

U.S. PATENT DOCUMENTS

2007/0046778 A1* 3/2007 Ishihara et al. ................. 348/68
2009/0147999 A1* 6/2009 Maeda et al. ................. 382/106

FOREIGN PATENT DOCUMENTS

JP    9-294706    11/1997
JP    2002-336187  11/2002

* cited by examiner

*Primary Examiner* — Kelly L Jerabek
(74) *Attorney, Agent, or Firm* — Scully, Scott, Murphy & Presser, P.C.

(57) ABSTRACT

An image processing device captures a normal light image of an observed region via a plurality of color filters having different spectral characteristics, respectively, generates a uniform image having low contrast by extracting each picture signal corresponding to a picture signal in a wavelength band for which light absorption characteristic of a contrast region in the observed region becomes low, and corrects each picture signal of a fluorescence image of the observed region by using the uniform image.

9 Claims, 17 Drawing Sheets

IMAGE PROCESSING DEVICE, IMAGING DEVICE, COMPUTER-READABLE DEVICE, AND IMAGE PROCESSING METHOD FOR PROCESSING A FLUORESCENCE IMAGE

CROSS-REFERENCE TO RELATED APPLICATIONS

This application is based upon and claims the benefit of priority from Japanese Patent Application No. 2009-077563, filed on Mar. 26, 2009, the entire contents of which are incorporated herein by reference.

BACKGROUND OF THE INVENTION

1. Field of the Invention

The present invention relates to an image processing device, an imaging device, a computer-readable recording medium recording an image processing program, and an image processing method, and particularly relates to an image processing device, an imaging device, a computer-readable recording medium recording an image processing program, and an image processing method for processing a fluorescence image based on fluorescence from a subject.

2. Description of the Related Art

Conventionally, endoscope apparatuses have been used in the medical field to observe inside of organs of a subject. The endoscope apparatuses generally capture a white light image of a body tissue by inserting an elongated flexible insertion portion into a body cavity of a subject such as a patient, applying white light to the body tissue in the body cavity via the inserted flexible insertion portion, and receiving reflected light by an imaging unit provided inside the flexible insertion portion. The white light image of the body tissue is displayed on a display unit of the endoscope apparatus. A user such as a doctor observes inside of the body cavity of the subject by using the white light image of the body tissue displayed on the display unit of the endoscope apparatus.

Meanwhile, in the field of endoscopes, there has been proposed in recent years an endoscope apparatus that is able to perform fluorescence observation of an observed region such as a body tissue inside a body cavity. Such a fluorescence-observation endoscope apparatus generally applies excitation light to the body tissue inside the body cavity via an inserted flexible insertion portion, and captures a fluorescence image of the observed region based on fluorescence generated from the body tissue.

When the observed region is a region in a luminal organ such as an esophagus or an intestine inside the subject, it is likely that an imaging distance between the observed region and the imaging unit of the endoscope apparatus is not constant. Therefore, when the imaging unit of the endoscope apparatus captures a fluorescence image of the observed region, light-dark contrast of fluorescence is caused because of variation in the imaging distance between the imaging unit and the observed region as an imaging object. The light-dark contrast of fluorescence makes it difficult to distinguish between a normal body tissue and an abnormal tissue during the fluorescence observation of the observed region.

To solve the problems mentioned above, the fluorescence-observation endoscope apparatus generates a standardization image based on light reflected from the observed region irradiated with light such as white light, performs a standardization process of dividing the fluorescence image of the observed region by the generated standardized image, and corrects lightness and darkness of the fluorescence caused by the above-described variation in the imaging distance between the imaging unit and the observed region. Then, the fluorescence-observation endoscope apparatus displays the fluorescence image, in which luminance values are standardized through the standardization process, on the display unit. A user such as a doctor observes the fluorescence image of the observed region displayed on the display unit of the fluorescence-observation endoscope apparatus, and makes a diagnosis of presence or absence of an abnormal tissue such as an affected area in the observed region inside the subject by the fluorescence observation.

When the observed region as an object of the above-described fluorescence observation contains a contrast region that forms contrast between light and dark (e.g., a blood vessel in a superficial layer or a deep blood vessel in a mucous membrane of the body tissue), a standardization image generated based on reflected light from the observed region contains, corresponding to the contrast region, a pixel portion having luminance largely different from that of a neighboring pixel, i.e., an edge. When the fluorescence image of the observed region is divided by the standardization image containing the edge, a luminance value of each pixel corresponding to the edge in the standardization image affects the standardization process, and an S/N ratio of the fluorescence image of the observed region may be decreased.

To prevent the decrease in the S/N ratio of the fluorescence image caused by the edge in the standardization image, there has been proposed an apparatus that performs a low-pass filter process on the standardization image based on the reflected light from the observed region, and divides the fluorescence image of the observed region by the standardization image subjected to the low-pass filter process (see, for example, Japanese Laid-open Patent Publication No. 2002-336187). Furthermore, there has been proposed an apparatus that captures a near-infrared light image of the observed region by applying near-infrared light to the observed region, and divides an image signal of the fluorescence image of the observed region by an image signal of the captured near-infrared light image (see, for example, Japanese Laid-open Patent Publication No. 09-294706).

SUMMARY OF THE INVENTION

An image processing device according to an aspect of the present invention includes a normal-light-image storage unit that stores therein each picture signal of a normal light image of an observed region, the normal light image being captured by a normal-light imaging unit that receives normal light from the observed region via a plurality of color filters having different spectral characteristics. The device also includes a fluorescence-image storage unit that stores therein each picture signal of a fluorescence image of the observed region, the fluorescence image being captured by a fluorescence imaging unit that receives fluorescence generated from the observed region irradiated with excitation light. The device also includes a uniform-image generating unit that extracts each picture signal corresponding to a specific color filter, which is one of the plurality of color filters and transmits light in a wavelength band for which a light absorption property of a contrast region in the observed region is low, from among each picture signal of the normal light image stored in the normal-light-image storage unit, and generates a uniform image of a wavelength-band component corresponding to the specific color filter based on each extracted picture signal. The device further includes a correction processing unit that corrects each picture signal of the fluorescence image stored in the fluorescence-image storage unit by using the uniform image.

An imaging device according to another aspect of the present invention includes a light source unit that switchably applies normal light and excitation light to an observed region. The device also includes a normal-light imaging unit that includes a plurality of color filters having different spectral characteristics and captures a normal light image of the observed region by receiving, via the plurality of color filters, normal light from the observed region irradiated with the normal light, and a fluorescence imaging unit that captures a fluorescence image of the observed region by receiving fluorescence generated from the observed region irradiated with the excitation light. The device also includes a uniform-image generating unit that extracts each picture signal corresponding to a specific color filter, which is one of the plurality of color filters and transmits light in a wavelength band for which a light absorption property of a contrast region in the observed region is low, from among each picture signal of the normal light image captured by the normal-light imaging unit, and generates a uniform image of a wavelength-band component corresponding to the specific color filter based on each extracted picture signal. The device further includes a correction processing unit that corrects each picture signal of the fluorescence image captured by the fluorescence imaging unit by using the uniform image.

A computer-readable medium according to another aspect of the present invention includes programmed instructions for performing an image processing, wherein the instructions, when executed by a computer, cause the computer to perform acquiring each picture signal of a normal light image of an observed region, the normal light image being captured by a normal-light imaging unit that receives normal light from the observed region via a plurality of color filters having different spectral characteristics, and each picture signal of a fluorescence image of the observed region, the fluorescence image being captured by a fluoresce imaging unit that receives fluorescence generated from the observed region irradiated with excitation light. The computer-readable medium also includes programmed instructions, wherein the instructions, when executed by a computer, cause the computer to perform extracting each picture signal corresponding to a specific color filter, which is one of the plurality of color filters and transmits light in a wavelength band for which a light absorption property of a contrast region in the observed region is low, and generating a uniform image of a wavelength-band component corresponding to the specific color filter based on each picture signal extracted at the extracting. The computer-readable medium further includes programmed instructions, wherein the instructions, when executed by a computer, cause the computer to perform correcting each picture signal of the fluorescence image by using the uniform image.

An image processing method according to still another aspect of the present invention includes acquiring each picture signal of a normal light image of an observed region, the normal light image being captured by a normal-light imaging unit that receives normal light from the observed region via a plurality of color filters having different spectral characteristics, and each picture signal of a fluorescence image of the observed region, the fluorescence image being captured by a fluoresce imaging unit that receives fluorescence generated from the observed region irradiated with excitation light. The method also includes extracting each picture signal corresponding to a specific color filter, which is one of the plurality of color filters and transmits light in a wavelength band for which a light absorption property of a contrast region in the observed region is low, and generating a uniform image of a wavelength-band component corresponding to the specific color filter based on each picture signal extracted at the extracting. The method further includes correcting each picture signal of the fluorescence image by using the uniform image.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Exemplary embodiments of an image processing device, an imaging device, a computer-readable recording medium recording an image processing program, and an image processing method according to the present invention will be explained in detail below with reference to the accompanying drawings. In the following embodiments, an endoscope apparatus that captures images of the inside of a body cavity of a subject such as a patient is described as an example of the imaging device of the present invention, and descriptions of an image processing device, a computer-readable recording medium recording an image processing program, and an image processing method used in the endoscope apparatus will be given subsequently. However, the present invention is not limited by the following embodiments.

First Embodiment

Figure 1:
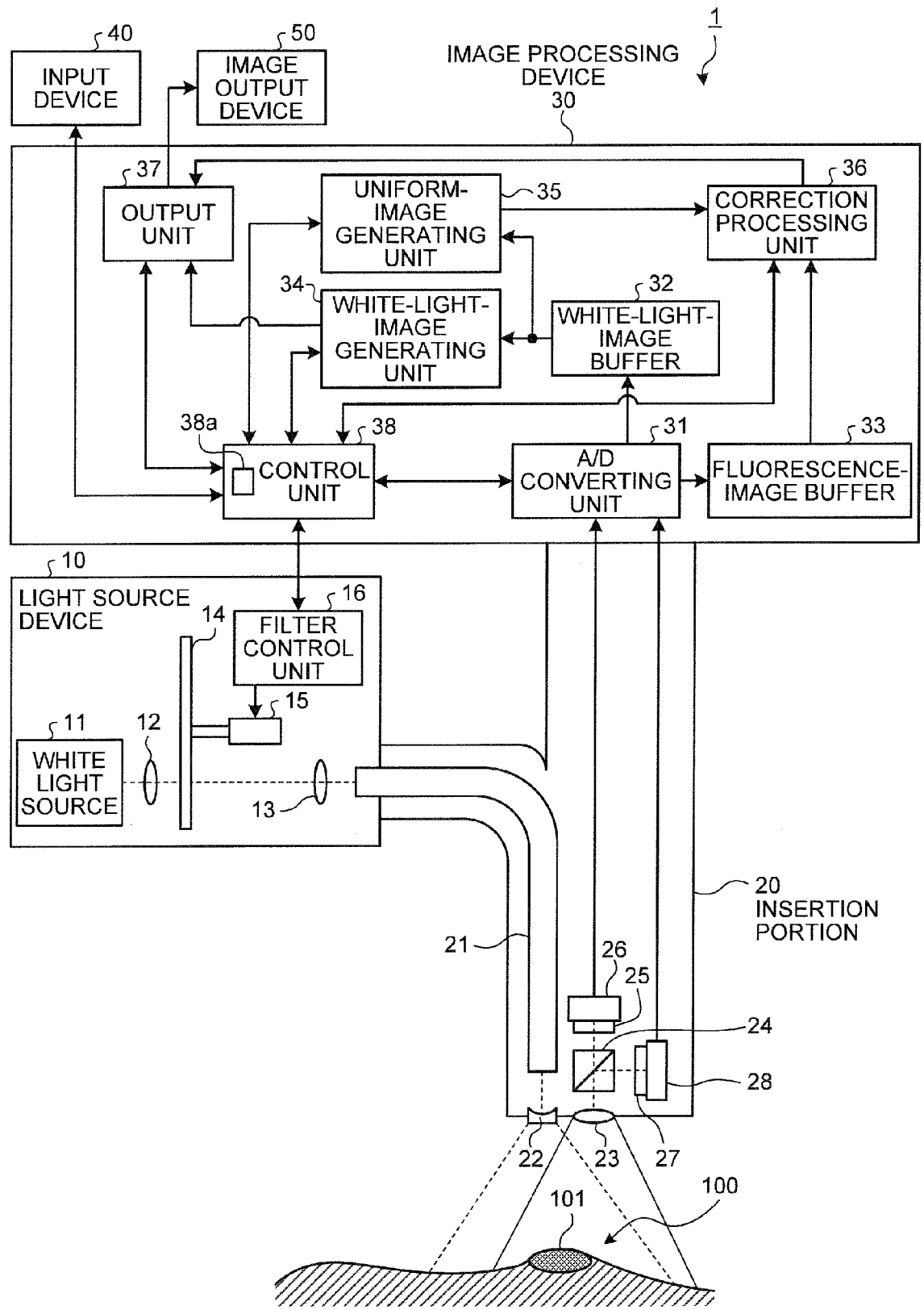
FIG. 1 is a block diagram schematically showing a configuration example of an endoscope apparatus according to a first embodiment of the present invention.

FIG. 1 is a block diagram schematically showing a configuration example of an endoscope apparatus according to a first embodiment of the present invention. An endoscope apparatus 1 according to the first embodiment is one example of the imaging device of the present invention. As illustrated in FIG. 1, the endoscope apparatus 1 includes a light source device 10 that applies light to an observed region 100 inside a subject, and an elongated insertion portion 20 to be inserted into a body cavity of the subject. The endoscope apparatus 1 also includes an image processing device 30 that processes images of the observed region 100, an input device 40 that inputs various types of information to the image processing device 30, and an image output device 50 that outputs image information processed by the image processing device 30.

The light source device 10 functions as a light source unit that switchably applies excitation light, which excites a fluorescent agent, and white light, which is one example of normal light, to the observed region 100. More specifically, the light source device 10 includes a white light source 11, a collimating lens 12 that collimates emission light from the white light source 11 into substantially parallel light, and a condensing lens 13 that condenses the parallel light. The light source device 10 also includes a rotary filter 14 that switches light applied to the observed region 100 between the excitation light and the white light, a motor 15 as a driving source of the rotary filter 14, and a filter control unit 16 that controls the rotary filter 14.

The white light source 11 is realized with use of a light emitting source such as a xenon lamp, and emits white light according to operation of a switch (not shown) of the light source device 10. The collimating lens 12 is disposed on an optical path of the white light to be emitted from the white light source 11, and collimates the white light from the white light source 11 into a substantially parallel light. The parallel light from the collimating lens 12 passes through the rotary filter 14, and is condensed by the condensing lens 13. The light condensed by the condensing lens 13 is applied to the observed region 100 inside the subject via the insertion portion 20.

Figure 2:
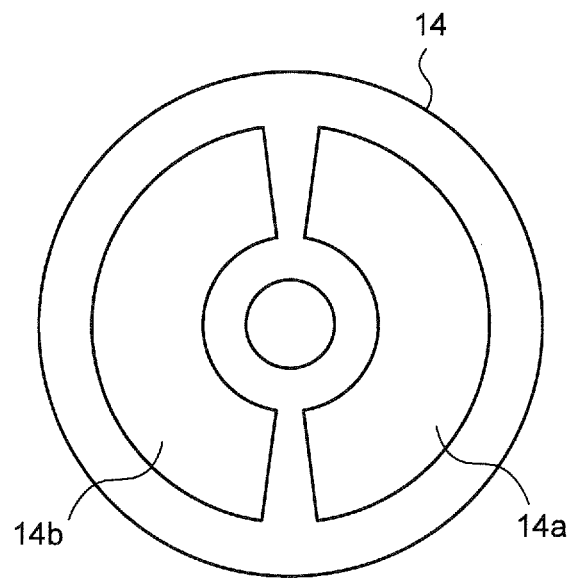
FIG. 2 is a schematic diagram illustrating a configuration example of a rotary filter according to the first embodiment.
Figure 3:
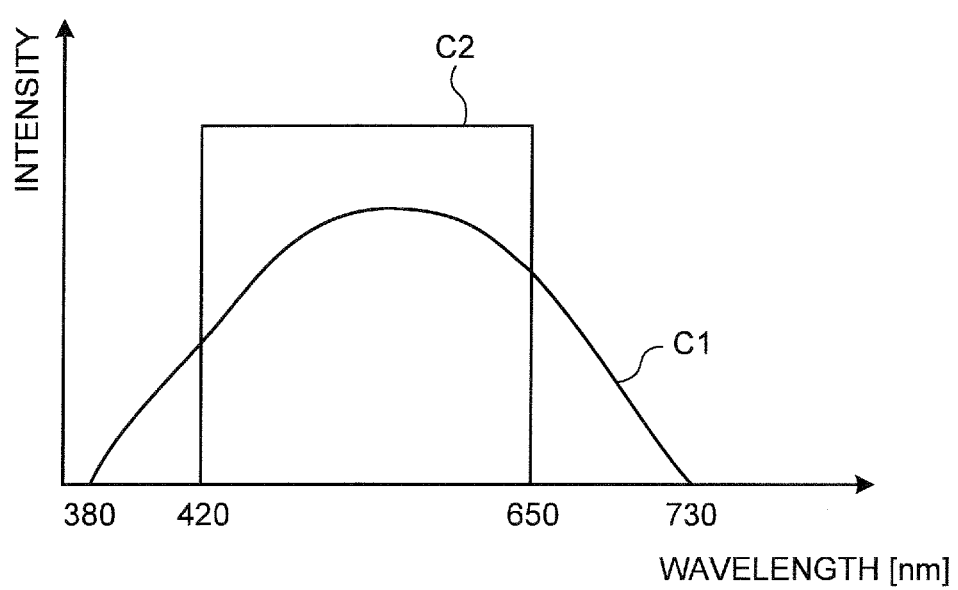
FIG. 3 is a schematic diagram illustrating an example of a spectral characteristic of a white light filter included in the rotary filter according to the first embodiment.
Figure 4:
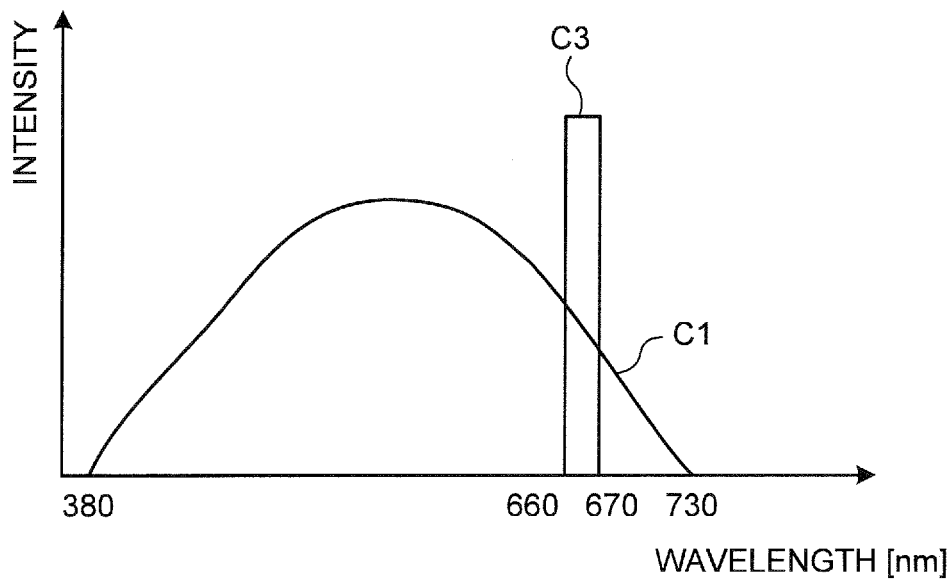
FIG. 4 is a schematic diagram illustrating an example of a spectral characteristic of an excitation light filter included in the rotary filter according to the first embodiment.

The rotary filter 14 extracts light in a predetermined wavelength band from the white light emitted from the white light source 11. FIG. 2 is a schematic diagram illustrating a configuration example of the rotary filter according to the first embodiment of the present invention. FIG. 3 is a schematic diagram illustrating an example of a spectral characteristic of a white light filter included in the rotary filter according to the first embodiment. FIG. 4 is a schematic diagram illustrating an example of a spectral characteristic of an excitation light filter included in the rotary filter according to the first embodiment. In FIGS. 3 and 4, a correlation line C1 of wavelength versus intensity is illustrated as an example of a spectral characteristic of the white light emitted from the white light source 11. The rotary filter 14 includes, as illustrated in FIG. 2, a white light filter 14a and an excitation light filter 14b that have different spectral characteristics.

The white light filter 14a transmits white light in a predetermined wavelength band within the white light emitted from the white light source 11. More specifically, the white light filter 14a has spectral transmittance with a 50%-transmission band of 420 nm to 650 nm as indicated by a correlation line C2 of wavelength versus intensity illustrated in FIG. 3. The 50%-transmission band of the white light filter 14a is a wavelength band of white light for which the spectral transmittance of the white light filter 14a becomes 50% or larger. The white light filter 14a having such spectral transmittance extracts white light in the wavelength band of 420 nm to 650 nm from the white light emitted from the white light source 11, i.e., the white light having the spectral characteristic indicated by the correlation line C1 of wavelength versus intensity illustrated in FIG. 3, and transmits the extracted white light as normal light to be applied to the observed region 100. A spectral characteristic of the white light transmitted through the white light filter 14a is calculated by multiplying the spectral characteristic of the white light from the white light source 11 (see the correlation line C1) by the spectral transmittance of the white light filter 14a (see the correlation line C2).

The excitation light filter 14b transmits excitation light in a predetermined wavelength band within the white light emitted from the white light source 11. More specifically, the excitation light filter 14b has spectral transmittance with a 50%-transmission band of 660 nm to 670 nm as indicated by a correlation line C3 of wavelength versus intensity illustrated in FIG. 4. The 500-transmission band of the excitation light filter 14b is a wavelength band of excitation light for which the spectral transmittance of the excitation light filter 14b becomes 50% or larger. The excitation light filter 14b having such spectral transmittance extracts excitation light being light in the wavelength band of 660 nm to 670 nm from the white light emitted from the white light source 11, i.e., the white light having the spectral characteristic indicated by the correlation line C1 of wavelength versus intensity illustrated in FIG. 4, and transmits the extracted excitation light. A spectral characteristic of the excitation light transmitted through the excitation light filter 14b is calculated by multiplying the spectral characteristic of the white light from the white light source 11 (see the correlation line C1) by the spectral transmittance of the excitation light filter 14b (see the correlation line C3).

The excitation light extracted by the excitation light filter 14b has properties of exciting a fluorescent agent specifically accumulated in, for example, an affected area 101 such as a tumor present in the observed region 100 and generating fluorescence in a wavelength band of, for example, 690 nm to 710 nm.

The rotary filter 14 having the white light filter 14a and the excitation light filter 14b as described above rotates in a circumferential direction with drive of the motor 15, so that the white light filter 14a and the excitation light filter 14b are switchably put in the optical path of the white light from the white light source 11 (see a dashed line in the light source device 10 illustrated in FIG. 1). The rotary filter 14 transmits white light of 420 nm to 650 nm when the white light filter 14a is put in the optical path, and transmits excitation light of 660 nm to 670 nm, which is out of the wavelength band of the transmitted white light, when the excitation light filter 14b is put in the optical path. In other words, the rotary filter 14 alternately transmits the white light and the excitation light.

The filter control unit 16 controls filter switching performed in the optical path by the rotation of the rotary filter 14 as described above. More specifically, the filter control unit 16 controls rotation drive of the motor 15 connected to the rotary filter 14 via an axis of rotation, and controls rotation drive of the rotary filter 14 through the drive control of the motor 15. Consequently, the filter control unit 16 alternately put the white light filter 14a and the excitation light filter 14b in the optical path of the white light from the white light source 11 as described above. In this manner, the filter control unit 16 controls the filter switching of the rotary filter 14 in the optical path. Furthermore, the filter control unit 16 recognizes whether the white light filter 14a or the excitation light filter 14b is put in the optical path based on a rotation drive condition such as a rotation frequency of the motor 15. The filter control unit 16 transmits to the image processing device 30 filter information indicating the filter (the white light filter 14a or the excitation light filter 14b) being put in the optical path. Operations of the filter control unit 16 are controlled by a control unit 38 of the image processing device 30 to be described later.

The insertion portion 20 is an elongated flexible structure insertable to a body cavity of a subject, and is bendable in a desired direction according to operation of an operating unit (not shown) of the endoscope apparatus 1. As illustrated in FIG. 1, the insertion portion 20 is connected to the light source device 10 and the image processing device 30 at its base end side. The insertion portion 20 includes a light guide fiber 21 that guides emission light from the light source device 10 toward its tip end side, and a lens 22 that diffuses the light guided by the light guide fiber 21. The insertion portion 20 also includes an objective lens 23 that collects normal light or fluorescence from the observed region 100, a dichroic mirror 24 that separates the focused light from the observed region 100, a white-light imaging unit 26 that captures a white light image of the observed region 100, and a fluorescence imaging unit 28 that captures a fluorescence image of the observed region 100. The white-light imaging unit 26 includes a color filter group 25 formed of a plurality of color filters having different spectral characteristics. The fluorescence imaging unit 28 includes a barrier filter 27 that transmits fluorescence from the observed region 100 and blocks excitation light from the observed region 100.

The light guide fiber 21 is realized with use of, for example, an optical fiber, and sequentially transmits the white light and the excitation light alternately emitted from the light source device 10 as described above toward the tip end side of the insertion portion 20. The white light and the excitation light emitted from the light source device 10 and sequentially guided by the light guide fiber 21 are sequentially diffused by the lens 22, and alternately applied to the observed region 100 inside the subject.

When the affected area 101 in which a fluorescent agent is accumulated in advance is present in the observed region 100, the excitation light applied from the light source device 10 to the observed region 100 excites the fluorescent agent in the affected area 101, so that fluorescence in a wavelength band of, for example, 690 nm to 710 nm is generated. In contrast, when the white light is applied from the light source device 10 to the observed region 100, white light, which is an example of normal light, is reflected by the observed region 100.

The objective lens 23 collects white light reflected by the observed region 100 when the white light is applied from the light source device 10 to the observed region 100. In contrast, when the excitation light is applied from the light source device 10 to the observed region 100, the objective lens 23 collects fluorescence generated from the observed region 100 (in particular, the fluorescence generated from the affected area 101) and excitation light reflected by the observed region 100.

The dichroic mirror 24 separates light coming from the observed region 100 and transmitted through the objective lens 23 into two lights, one of which is toward the white-light imaging unit 26 side and the other one of which is toward the fluorescence imaging unit 28 side. More specifically, the dichroic mirror 24 separates, from the light coming from the observed region 100 and collected by the objective lens 23 described above, light in a wavelength band shorter than 660 nm, i.e., white light reflected by the observed region 100 (e.g., white light of 420 nm to 650 nm) toward an optical path on the white-light imaging unit 26 side. On the other hand, the dichroic mirror 24 has a function of reflecting 100% of light in a wavelength band equal to or longer than 660 nm, and separates the fluorescence generated from the observed region 100 and the excitation light reflected by the observed region 100 toward an optical path on the fluorescence imaging unit 28 side. A wavelength band of the excitation light reflected by the observed region 100 is from 660 nm to 670 nm for example, and a wavelength band of the fluorescence from the observed region 100 is from 690 nm to 710 nm for example.

Figure 5:
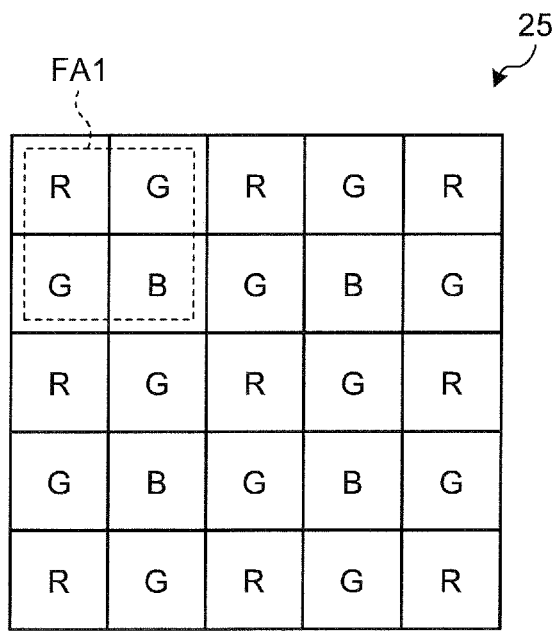
FIG. 5 is a schematic diagram illustrating a configuration example of a color filter group arranged on a light receiving surface of a white-light imaging unit according to the first embodiment.
Figure 6:
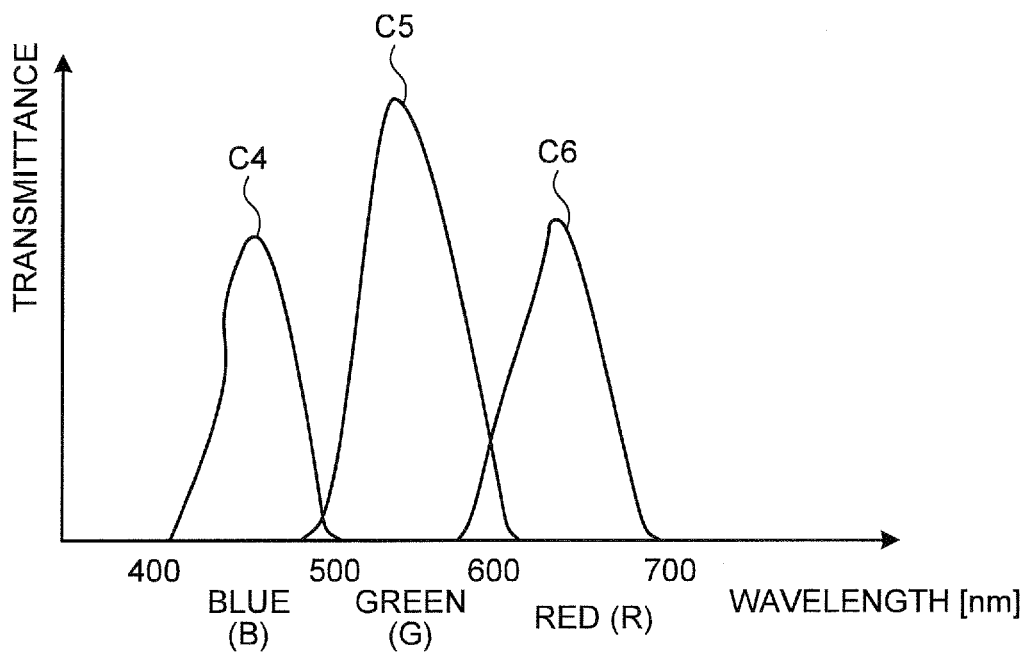
FIG. 6 is a schematic diagram illustrating an example of transmittance properties of the color filter group according to the first embodiment.

The color filter group 25 is formed of the plurality of color filters having different spectral characteristics. The color filter group 25 splits the white light from the observed region 100 into light of each color component for each pixel of the white-light imaging unit 26, and transmits the light of each color component toward each pixel of the white-light imaging unit 26. FIG. 5 is a schematic diagram illustrating a configuration example of the color filter group arranged on a light receiving surface of the white-light imaging unit according to the first embodiment. FIG. 6 is a schematic diagram illustrating an example of transmittance properties of the color filter group according to the first embodiment. The color filter group 25 is, as illustrated in FIG. 5 for example, a primary color filter in the form of mosaic containing a plurality of red light filters (R) being color filters that transmit red light, a plurality of green light filters (G) being color filters that transmit green light, and a plurality of blue light filters (B) being color filters that transmit blue light. A color filter assembly FA1 of 2×2 is a base unit of the color filter group 25. At least one red light filter, one green light filter, and one blue light filter are contained in the base unit.

In the color filter group 25, the blue light filters have spectral transmittance to transmit light in a wavelength band of 400 nm to 500 nm as indicated by a correlation line C4 of wavelength versus transmittance illustrated in FIG. 6. The green light filters have spectral transmittance to transmit light in a wavelength band of 480 nm to 600 nm as indicated by a correlation line C5 of wavelength versus transmittance illustrated in FIG. 6. The red light filters have spectral transmittance to transmit light in a wavelength band of 580 nm to 700 nm as indicated by a correlation line C6 of wavelength versus transmittance illustrated in FIG. 6. In the color filter group 25, a wavelength band of blue light for which the spectral transmittance of the blue light filters becomes 50% or larger (i.e., the 50%-transmission band of the blue light filters) is from 430 nm to 480 nm; a wavelength band of green light for which the spectral transmittance of the green light filters becomes 50% or larger (i.e., the 50%-transmission band of the green light filters) is from 510 nm to 580 nm; and a wavelength band of red light for which the spectral transmittance of the red light filters becomes 50% or larger (i.e., the 50%-transmission band of the red light filters) is from 600 nm to 680 nm.

The color filter group 25 structured as described above extracts, from the white light coming from the observed region 100 and separated toward the optical path on the white-light imaging unit 26 side by the dichroic mirror 24, blue light of 430 nm to 480 nm for example by the blue light filters, green light of 510 nm to 580 nm for example by the green light filters, and red light of 600 nm to 680 nm for example by the red light filters. Each blue light filter in the color filter group 25 transmits a blue component of the white light toward each pixel corresponding to blue in the white-light imaging unit 26. Each green light filter in the color filter group 25 transmits a green component of the white light toward each pixel corresponding to green in the white-light imaging unit 26. Each red light filter in the color filter group 25 transmits a red component of the white light toward each pixel corresponding to red in the white-light imaging unit 26.

The color filter assembly FA1 of 2×2 as the base unit of the color filter group 25 contains at least one red light filter (R), one green light filter (G), and one blue light filter (B) as described above, but the size of the color filter group 25 is not limited by 5×5 as illustrated in FIG. 5. In other words, the color filter group 25 may be formed in a desired size with a desired number of color filters depending on the light receiving surface of the white-light imaging unit 26.

The white-light imaging unit 26 is realized with use of a Bayer-type color imaging element in which color filters having different spectral characteristics are arranged on pixels in the light receiving element. More specifically, the white-light imaging unit 26 includes an infrared-light cut filter (not shown) that removes infrared light and the color filter group 25 described above on the light receiving surface. A light receiving portion of the white-light imaging unit 26 is formed with use of, for example, a pixel assembly of 2×2 as a base unit, and is constructed of a pixel group containing a plurality of the pixel assemblies each being the base unit. In the light receiving portion of the white-light imaging unit 26, the color filter assembly FA1 as the base unit of the color filter group 25 described above is arranged for each pixel assembly being the base unit. In other words, one or more red light filters, one or more green light filters, and one or more blue light filters in the color filter assembly FA1 being the base unit of the color filter group 25 are provided on the pixel assembly being the base unit of the white-light imaging unit 26.

The white-light imaging unit 26 structured as described above receives, via the above-mentioned color filter group 25, normal light coming from the observed region 100 and separated toward the optical path on the white-light imaging unit 26 side by the dichroic mirror 24, i.e., white light reflected by the observed region 100 when the white light is applied from the light source device 10 to the observed region 100. Accordingly, the white-light imaging unit 26 captures a white light image being a color image of the observed region 100. In this case, the white-light imaging unit 26 causes each pixel in the pixel group to perform a photoelectric conversion process on the normal light of each color component split from the white light by the color filter group 25 and generate a picture signal of each color component constituting the white light image of the observed region 100.

The pixel group in the light receiving portion of the white-light imaging unit 26 is formed of a plurality of blue pixels being pixels on which the blue light filters of the color filter group 25 are arranged, a plurality of green pixels being pixels on which the green light filters of the color filter group 25 are arranged, and a plurality of red pixels being pixels on which the red light filters of the color filter group 25 are arranged. In the pixel group of the white-light imaging unit 26, the blue pixels receive normal light of a blue component (in a wavelength band of 430 nm to 480 nm for example) transmitted through the blue light filters from the white light coming from the observed region 100, and perform the photoelectric conversion process on the received normal light of the blue component to thereby generate a picture signal of the blue component of the observed region 100 (hereinafter, referred to as "B picture signal"). The green pixels receive normal light of a green component (in a wavelength band of 510 nm to 580 nm for example) transmitted through the green light filters from the white light coming from the observed region 100, and perform the photoelectric conversion process on the received normal light of the green component to thereby generate a picture signal of the green component of the observed region 100 (hereinafter, referred to as "G picture signal"). The red pixels receive normal light of a red component (in a wavelength band of 600 nm to 680 nm for example) transmitted through the red light filters from the white light coming from the observed region 100, and perform the photoelectric conversion process on the received normal light of the red component to thereby generate a picture signal of the red component of the observed region 100 (hereinafter, referred to as "R picture signal"). As described above, the white-light imaging unit 26 sequentially transmits to the image processing device 30 each B picture signal, each G picture signal, and each R picture signal constituting the white light image of the observed region 100 every time the white-light imaging unit 26 captures the white light image of the observed region 100.

Figure 7:
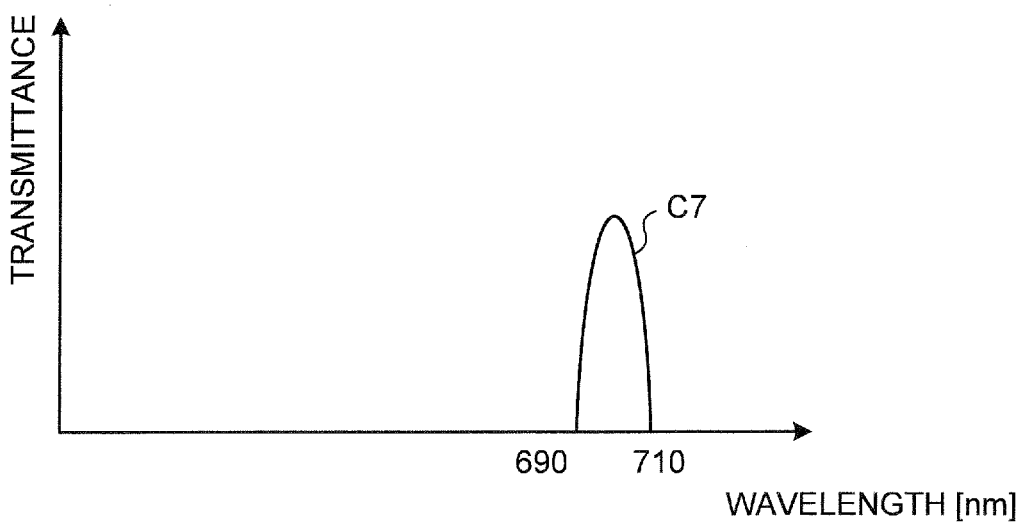
FIG. 7 is a schematic diagram illustrating an example of a transmittance property of a barrier filter according to the first embodiment.

The barrier filter 27 is realized with use of an excitation-light cut filter, and blocks excitation light contained in the light, which is coming from the observed region 100 and separated toward the optical path on the fluorescence imaging unit 28 side by the dichroic mirror 24. FIG. 7 is a schematic diagram illustrating an example of a transmittance property of the barrier filter. The barrier filter 27 has a spectral characteristic to transmit light in a wavelength band of 690 nm to 710 nm as indicated by a correlation line C7 of wavelength versus transmittance illustrated in FIG. 7. The barrier filter 27 blocks excitation light reflected by the observed region 100 (excitation light in a wavelength band of 660 nm to 670 nm for example) with respect to the light coming from the observed region 100 and separated toward the optical path on the fluorescence imaging unit 28 by the dichroic mirror 24, and transmits fluorescence which is light in a wavelength band of 690 nm to 710 nm and coming from the observed region 100.

The fluorescence imaging unit 28 is realized with use of a monochrome imaging element having higher sensitivity than that of the white-light imaging unit 26, and includes the barrier filter 27 described above on its light receiving surface. The fluorescence imaging unit 28 receives, when the light source device 10 applies excitation light to the observed region 100, fluorescence coming from the observed region 100 and separated toward the optical path on the fluorescence imaging unit 28 side by the dichroic mirror 24, i.e., fluorescence transmitted through the barrier filter 27. Accordingly, the fluorescence imaging unit 28 captures a fluorescence image of the observed region 100. In this case, the fluorescence imaging unit 28 causes each pixel in the light receiving portion to perform a photoelectric conversion process on the fluorescence from the observed region 100 and generate each picture signal constituting the fluorescence image of the observed region 100. The fluorescence imaging unit 28 sequentially transmits each picture signal of the fluorescence image of the observed region 100 to the image processing device 30 every time the fluorescence imaging unit 28 captures the fluorescence image of the observed region 100. Brightness and darkness of the fluorescence in the fluorescence image of the observed region 100 captured by the fluorescence imaging unit 28 vary depending on an imaging distance between the observed region 100 as an imaging object and the fluorescence imaging unit 28.

The image processing device 30 processes image information of the observed region 100 captured by the white-light imaging unit 26 or the fluorescence imaging unit 28 described above, and generates an output image to be output to the image output device 50. More specifically, as illustrated in FIG. 1, the image processing device 30 includes an A/D converting unit 31 that converts each picture signal captured by the white-light imaging unit 26 or the fluorescence imaging unit 28 from an analog signal to a digital signal, a white-light-image buffer 32 that temporarily stores therein each picture signal of a white light image captured by the white-light imaging unit 26, and a fluorescence-image buffer 33 that temporarily stores therein each picture signal of a fluorescence image captured by the fluorescence imaging unit 28. The image processing device 30 also includes a white-light-image generating unit 34 that generates a white light image of the observed region 100, a uniform-image generating unit 35 that generates a uniform image used for a correction process of a fluorescence image of the observed region 100, and a correction processing unit 36 that performs the correction process on the fluorescence image of the observed region 100 based on the uniform image generated based on the picture signal of the observed region 100. The image processing device 30 also includes an output unit 37 that outputs image information to the image output device 50 and the control unit 38 that controls each component of the image processing device 30.

In the image processing device 30, the A/D converting unit 31 is connected to the white-light-image buffer 32 and the fluorescence-image buffer 33. The A/D converting unit 31 is also connected to the white-light imaging unit 26 and the fluorescence imaging unit 28 described above. The white-light-image buffer 32 is connected to the white-light-image generating unit 34 and the uniform-image generating unit 35. The correction processing unit 36 is connected to the fluorescence-image buffer 33 and the uniform-image generating unit 35. The output unit 37 is connected to the white-light-image generating unit 34 and the correction processing unit 36. The output unit 37 is also connected to the image output device 50. The control unit 38 is connected interactively to the A/D converting unit 31, the white-light-image generating unit 34, the uniform-image generating unit 35, the correction processing unit 36, and the output unit 37. The control unit 38 is also connected interactively to the filter control unit 16 of the light source device 10 described above and the input device 40.

The A/D converting unit 31 converts a picture signal acquired from the white-light imaging unit 26 or the fluorescence imaging unit 28 from an analog signal to a digital signal, and sends the digitalized picture signal to the white-light-image buffer 32 or the fluorescence-image buffer 33. More specifically, when the light source device 10 described above applies white light to the observed region 100, the A/D converting unit 31 acquires each B picture signal, each G picture signal, and each R picture signal of the white light image of the observed region 100 from the white-light imaging unit 26. In this case, the A/D converting unit 31 digitalizes the acquired B picture signals, G picture signals, and R picture signals of the white light image, and sequentially sends the digitalized B picture signals, G picture signals, and R picture signals to the white-light-image buffer 32 with control by the control unit 38. In contrast, when the light source device 10 described above applies excitation light to the observed region 100, the A/D converting unit 31 acquires each picture signal of the fluorescence image of the observed region 100 from the fluorescence imaging unit 28. In this case, the A/D converting unit 31 digitalizes each acquired picture signal of the fluorescence image, and sequentially sends each digitalized picture signal to the fluorescence-image buffer 33 with control by the control unit 38.

The white-light-image buffer 32 functions as a normal-light-image storage unit for storing each picture signal of a normal light image of the observed region 100 captured by the white-light imaging unit 26 described above. More specifically, the white-light-image buffer 32 acquires each picture signal of the white light image, which has been digitalized by the A/D converting unit 31, i.e., the digitalized B picture signals, G picture signals, and R picture signals, from the A/D converting unit 31. The white-light-image buffer 32 temporarily stores therein the digitalized B picture signals, G picture signals, and R picture signals acquired from the A/D converting unit 31. Then, the white-light-image buffer 32 appropriately sends the temporarily-stored digitalized B picture signals, G picture signals, and R picture signals to the white-light-image generating unit 34 and the uniform-image generating unit 35.

The fluorescence-image buffer 33 functions as a fluorescence-image storage unit for storing each picture signal of a fluorescence image of the observed region 100 captured by the fluorescence imaging unit 28 described above. More specifically, the fluorescence-image buffer 33 acquires each picture signal of the fluorescence image, which has been digitalized by the A/D converting unit 31, and temporarily stores therein the digitalized picture signals acquired from the A/D converting unit 31. Then, the fluorescence-image buffer 33 appropriately sends the temporarily-stored digitalized picture signals to the correction processing unit 36.

The white-light-image generating unit 34 generates a white light image of the observed region 100 based on each picture signal of one frame temporarily stored in the white-light-image buffer 32. More specifically, the white-light-image generating unit 34 acquires each B picture signal, each G picture signal, and each R picture signal, which are of a single-chip imaging element and correspond to one frame of the white light image, from the white-light-image buffer 32. The white-light-image generating unit 34 performs an interpolation process of the acquired B picture signals, G picture signals, and R picture signals which are of the single-chip imaging element. Consequently, the white-light-image generating unit 34 generates a picture signal corresponding to three-chip imaging elements, in which the color components contained in the pixel assembly being the base unit described above are combined with each other, for each pixel assembly being the base unit. The white-light-image generating unit 34 performs a color conversion process, a tone conversion process, and the like on each picture signal corresponding to the three-chip imaging elements generated as described above to thereby generate the white light image of the observed region 100. The white-light-image generating unit 34 sequentially performs the above-mentioned image processing to generate the white light image of the observed region 100 frame by frame every time the white-light-image generating unit 34 acquires each picture signal of the white light image of one frame from the white-light-image buffer 32. The white-light-image generating unit 34 sequentially sends each picture signal of the white light image of the observed region 100 generated as described above to the output unit 37.

The uniform-image generating unit 35 generates a uniform image to be used for a correction process of correcting each picture signal of the fluorescence image of the observed region 100 captured by the fluorescence imaging unit 28 described above. More specifically, the uniform-image generating unit 35 acquires each picture signal of the white light image of the observed region 100 stored in the white-light-image buffer 32, e.g., each B picture signal, each G picture signal, and each R picture signal of one frame. The uniform-image generating unit 35 extracts, from among the picture signals of the white light image acquired from the white-light-image buffer 32, each picture signal corresponding to a specific color filter, which is contained in the color filter group 25 described above and transmits light in a wavelength band for which a light absorption property of a contrast region in the observed region 100 is low. Then, the uniform-image generating unit 35 generates a uniform image of a wavelength-band component (a red component for example) corresponding to the specific color filter based on the extracted picture signals. The uniform-image generating unit 35 sequentially sends each picture signal of the uniform image generated as described above to the correction processing unit 36.

The above-mentioned contrast region is a region that forms contrast between light and dark in the observed region 100. For example, when the observed region 100 is a region in a body cavity, the contrast region in the observed region 100 may be a microscopic structure such as a capillary in a superficial layer of a mucous membrane of a body tissue or a deep blood vessel in a body tissue. In this case, the white light image of the observed region 100 contains, corresponding to the contrast region, a pixel portion having luminance largely different from that of neighboring pixels, i.e., an edge. The uniform image generated by the uniform-image generating unit 35 described above is a substantially uniform image of a wavelength-band component such as the red component corresponding to the specific color filter, and the contrast caused by the edge is reduced in this image.

The correction processing unit 36 performs the correction process on each picture signal of the fluorescence image of the observed region 100 captured by the fluorescence imaging unit 28 described above. More specifically, the correction processing unit 36 acquires each picture signal of the fluorescence image of the observed region 100 stored in the fluorescence-image buffer 33, and each picture signal of the uniform image of the observed region 100 generated by the uniform-image generating unit 35. The uniform image of the observed region 100 described herein is a uniform image generated based on each picture signal of a specific wavelength-band component selected from among the picture signals of the white light image of the observed region 100. The correction processing unit 36 performs the correction process on each picture signal of the fluorescence image of the observed region 100 based on the picture signals of the uniform image of the observed region 100 acquired from the uniform-image generating unit 35. Consequently, the correction processing unit 36 generates a fluorescence image in which the lightness and darkness of fluorescence that vary depending on the imaging distance between the observed region 100 and the fluorescence imaging unit 28 is corrected. In the fluorescence image of the observed region 100 obtained through the correction process by the correction processing unit 36, the affected area 101 as a source of generating fluorescence upon irradiation with the excitation light is drawn by pixels with relatively high luminance regardless of the imaging distance between the observed region 100 and the fluorescence imaging unit 28. The correction processing unit 36 sequentially sends each picture signal of the fluorescence image obtained by the correction process to the output unit 37.

The output unit 37 outputs image information of the observed region 100 to the image output device 50. More specifically, the output unit 37 acquires each picture signal of the white light image of the observed region 100 generated by the white-light-image generating unit 34 and each picture signal of the fluorescence image of the observed region 100 obtained through the correction process by the correction processing unit 36. The output unit 37 sequentially outputs each picture signal of the white light image and the fluorescence image of the observed region 100 to the image output device 50 with control by the control unit 38. Consequently, the output unit 37 outputs (displays for example) the white light image of the observed region 100 and the fluorescence image of the observed region 100 obtained by the correction process onto the image output device 50.

The control unit 38 controls operations of the A/D converting unit 31, the white-light-image generating unit 34, the uniform-image generating unit 35, the correction processing unit 36, and the output unit 37, which are components of the image processing device 30, and also controls input and output of signals between the components. Furthermore, the control unit 38 controls the filter control unit 16 of the light source device 10 described above and the input device 40.

More specifically, the control unit 38 is realized with use of a storage unit 38a for storing a predetermined processing program including an image processing program, and a computer that executes the processing program stored in the storage unit 38a. The control unit 38 sets various imaging conditions for capturing the white light image and the fluorescence image of the observed region 100 based on setting information input from the input device 40. Furthermore, the control unit 38 controls the filter control unit 16 to control the filter switching of the rotary filter 14 described above based on instruction information input from the input device 40.

The control unit 38 sequentially acquires the filter information described above from the filter control unit 16. The control unit 38 identifies based on the filter information whether the filter of the rotary filter 14 being put in the optical path of the light source device 10 is the white light filter 14a or the excitation light filter 14b. When the filter in the optical path of the light source device 10 is the white light filter 14a, the control unit 38 acquires each picture signal of the white light image from the white-light imaging unit 26 and controls the A/D converting unit 31 to digitalize each picture signal of the white light image. When the filter in the optical path of the light source device 10 is not the white light filter 14a, the control unit 38 controls the A/D converting unit 31 to delete a picture signal obtained from the white-light imaging unit 26. By controlling the A/D converting unit 31, the control unit 38 controls the white-light imaging unit 26 so that timing to apply the white light to the observed region 100 by the light source device 10 and timing to capture the white light image by the white-light imaging unit 26 are synchronized with each other.

In contrast, when the filter in the optical path of the light source device 10 is the excitation light filter 14b, the control unit 38 acquires each picture signal of the fluorescence image from the fluorescence imaging unit 28 and controls the A/D converting unit 31 to digitalize each picture signal of the fluorescence image. When the filter in the optical path of the light source device 10 is not the excitation light filter 14b, the control unit 38 controls the A/D converting unit 31 to delete a picture signal obtained from the fluorescence imaging unit 28. By controlling the A/D converting unit 31, the control unit 38 controls the fluorescence imaging unit 28 so that timing to apply the excitation light to the observed region 100 by the light source device 10 and timing to capture the fluorescence image by the fluorescence imaging unit 28 are synchronized with each other.

The control unit 38 controls the white-light-image generating unit 34 to generate the white light image of the observed region 100 based on each picture signal of the single-chip imaging element corresponding to the observed region 100, and also controls the uniform-image generating unit 35 to generate the uniform image of the observed region 100 based on each picture signal in a specific wavelength band extracted from among the picture signals of the single-chip imaging element. Furthermore, the control unit 38 controls the correction processing unit 36 to perform the correction process on each picture signal of the fluorescence image of the observed region 100 based on the uniform image of the observed region 100. The control unit 38 also controls the output unit 37 to output each picture signal of the white light image of the observed region 100 and each picture signal of the fluorescence image of the observed region 100 obtained by the correction process to the image output device 50, based on instruction information input from the input device 40. By controlling the output unit 37, the control unit 38 controls operations of outputting the white light image and the fluorescence image of the observed region 100 by the image output device 50.

The input device 40 is realized with use of an input device such as a keyboard and a mouse, and inputs various types of information to the control unit 38 of the image processing device 30 in accordance with input operations by a user such as a doctor or a nurse. The various types of information to be input to the control unit 38 by the input device 40 may be instruction information for instructing the control unit 38 to start rotating the rotary filter 14 or start outputting the white light image and the fluorescence image of the observed region 100, and various types of setting information for capturing the white light image or the fluorescence image of the observed region 100. The input device 40 may be provided with a power switch for switching on and off the image processing device 30 described above.

The image output device 50 outputs the image information processed by the image processing device 30 described above. More specifically, the image output device 50 is realized with use of a desired display such as a CRT display and a liquid crystal display. The image output device 50 acquires image information of the observed region 100, i.e., each picture signal of the white light image and each picture signal of the fluorescence image obtained by the correction process, from the output unit 37 of the image processing device 30. The image output device 50 displays the white light image and the fluorescence image of the observed region 100 obtained by the correction process, based on each picture signal acquired from the output unit 37. In this case, the image output device 50 is allowed to display the white light image and the fluorescence image of the observed region 100 obtained by the correction process side-by-side, or to display the white light image and the fluorescence image of the observed region 100 obtained by the correction process such that they overlap each other.

Figure 8:
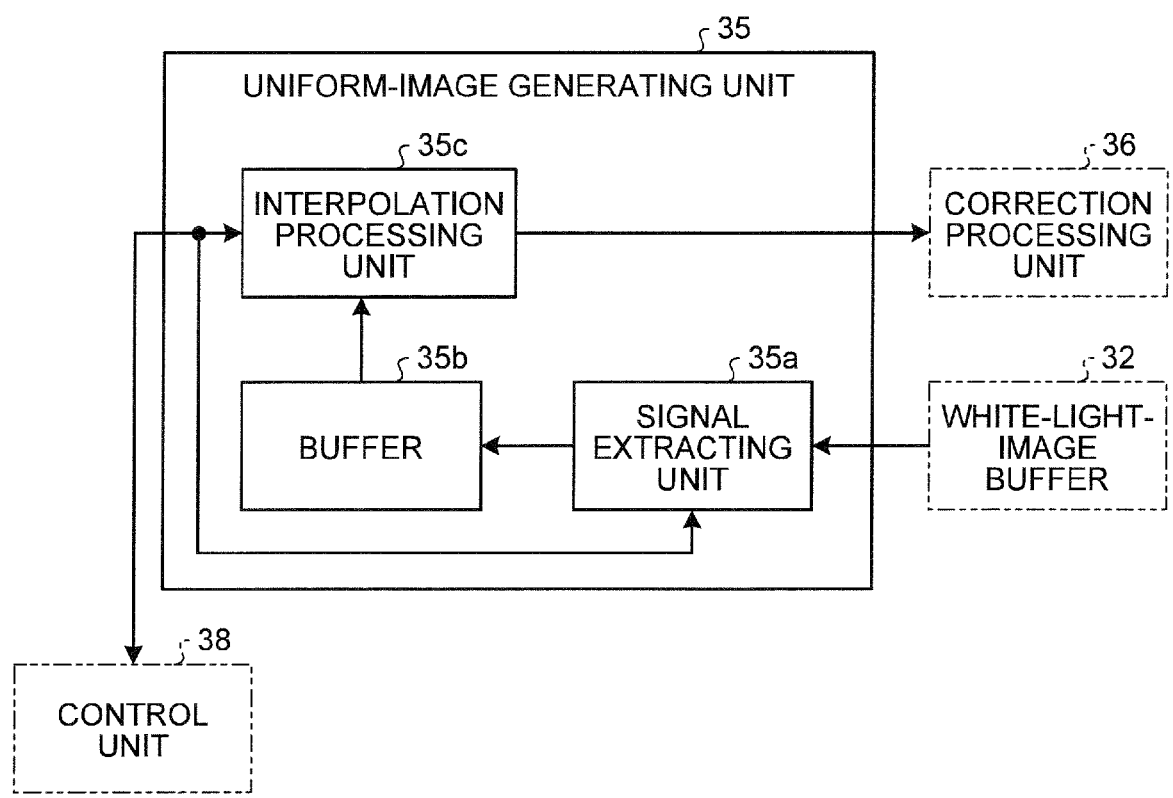
FIG. 8 is a block diagram schematically showing a configuration example of a uniform-image generating unit of an image processing device according to the first embodiment.

Next, the uniform-image generating unit 35 of the above-mentioned image processing device 30 is described in detail below. FIG. 8 is a block diagram schematically showing a configuration example of the uniform-image generating unit of the image processing device according to the first embodiment. As illustrated in FIG. 8, the uniform-image generating unit 35 includes a signal extracting unit 35a that extracts a picture signal in a specific wavelength band from among picture signals of the white light image, a buffer 35b that temporarily stores therein the picture signal extracted by the signal extracting unit 35a, and an interpolation processing unit 35c that generates the above-mentioned uniform image by performing the interpolation process of each picture signal extracted by the signal extracting unit 35a.

The signal extracting unit 35a extracts, from among the picture signals of the white light image stored in the white-light-image buffer 32, each picture signal corresponding to the specific color filter in the color filter group 25 of the white-light imaging unit 26 described above, with control by the control unit 38. More specifically, the signal extracting unit 35a extracts each R picture signal corresponding to the red light filter in the color filter group 25 from among each B picture signal, each G picture signal, and each R picture signal of one frame constituting the white light image of the observed region 100. In this case, the signal extracting unit 35a performs a process of thinning out each B picture signal corresponding to the blue light filters of the color filter group 25 and each G picture signal corresponding to the green light filters of the color filter group 25. Among the blue light filter, the green light filter, and the red light filter contained in the color filter group 25, the red light filter is described as an example of the specific color filter that transmits light in a wavelength band for which the light absorption property of the contrast region (e.g., a blood vessel) present in the observed region 100 such as a body tissue is comparatively low. The signal extracting unit 35a extracts each R picture signal corresponding to the red light filter being the specific color filter, from among the picture signals of the white light image of the observed region 100 stored in the white-light-image buffer 32, i.e., the B picture signals, the G picture signals, and the R picture signals of the single-chip imaging element. The signal extracting unit 35a sequentially sends each R picture signal of the single-chip imaging element extracted as described above to the buffer 35b with control by the control unit 38.

Herein, the light in the wavelength band for which the light absorption property is comparatively low is light in a wavelength band for which light absorptance of the contrast region becomes lower than the light absorptance at other wavelength bands. The light in the wavelength band for which the light absorption property of the contrast region is low may be light in a wavelength band for which the absorptance is smaller than a predetermined threshold, or may be light in a wavelength band for which the absorptance is smaller average absorptance of the light absorption property of the contrast region. Furthermore, the light in the wavelength band for which the light absorption property of the contrast region is low may be light in arbitrary wavelength bands determined by experiments.

The buffer 35b acquires each picture signal in the specific wavelength band extracted by the signal extracting unit 35a, i.e., each R picture signal of the single-chip imaging element, and temporarily stores therein each R picture signal of the single-chip imaging element acquired from the signal extracting unit 35a. Then, the buffer 35b appropriately sends each temporarily-stored R picture signal of the single-chip imaging element to the interpolation processing unit 35c.

The interpolation processing unit 35c performs the interpolation process of each picture signal in the specific wavelength band extracted by the signal extracting unit 35a, and generates a uniform image of a wavelength-band component corresponding to the specific color filter in the color filter group 25 described above. More specifically, the interpolation processing unit 35c acquires from the buffer 35b each R picture signal of the single-chip imaging element, which is a picture signal in the specific wavelength band extracted by the signal extracting unit 35a, and performs the interpolation process of each acquired R picture signal of the single-chip imaging element, with control by the control unit 38. By performing the interpolation process of each R picture signal, the interpolation processing unit 35c allocates the R picture signals to respective spaces of the B picture signals and the G picture signals which have been thinned out during the process of extracting each R picture signal by the signal extracting unit 35a described above. Consequently, the interpolation processing unit 35c generates the uniform image of each R picture signal of one frame corresponding to the red light filter being the specific color filter described above, i.e., the uniform image of the red component being the wavelength-band component corresponding to the red light filter. The interpolation processing unit 35c sequentially sends each picture signal (in particular, each R picture signal) of the generated uniform image to the correction processing unit 36, with control by the control unit 38.

Figure 9:
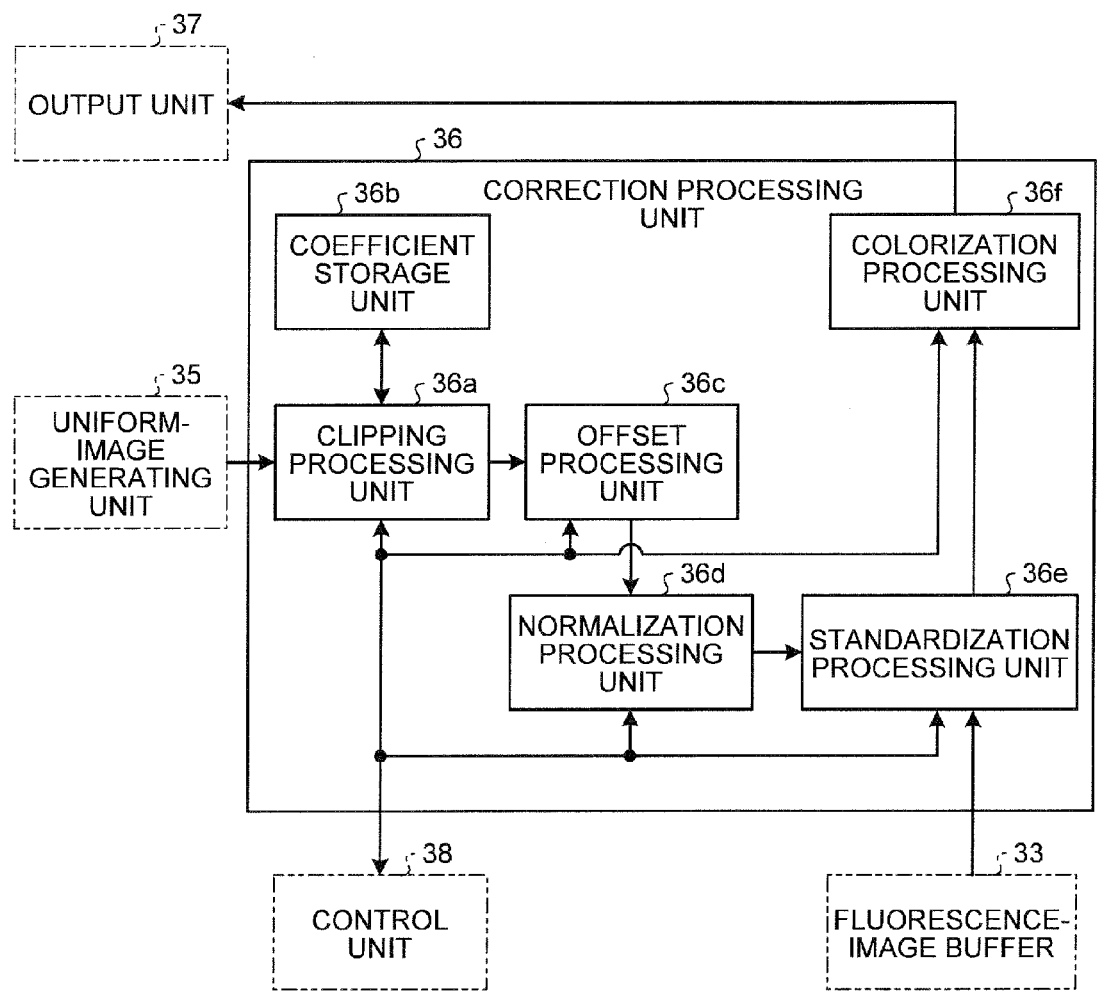
FIG. 9 is a block diagram schematically showing a configuration example of a correction processing unit of the image processing device according to the first embodiment.

Next, the correction processing unit 36 of the above-mentioned image processing device 30 is described in detail below. FIG. 9 is a block diagram schematically showing a configuration example of the correction processing unit of the image processing device according to the first embodiment of the present invention. As illustrated in FIG. 9, the correction processing unit 36 includes a clipping processing unit 36a the performs a clipping process on each picture signal of the uniform image, a coefficient storage unit 36b that stores therein in advance a clipping coefficient used for the clipping process, and an offset processing unit 36c that uniformly adds a predetermined value to each picture signal of the uniform image. The correction processing unit 36 also includes a normalization processing unit 36d that performs a normalization process on each picture signal of the uniform image, a standardization processing unit 36e that corrects each picture signal of the fluorescence image of the observed region 100 by a standardization process, and a colorization processing unit 36f that performs a colorization process on the fluorescence image after the standardization process. As will be described later, the correction processing unit 36 corrects each picture signal of the fluorescence image of the observed region 100 based on the uniform image obtained by completion of the clipping process, the offset process, and the normalization process, and subsequently performs the colorization process on the fluorescence image obtained by completion of the correction process.

The clipping processing unit 36a performs the clipping process on each picture signal of the uniform image generated by the uniform-image generating unit 35. More specifically, the clipping processing unit 36a acquires each picture signal of the uniform image of the observed region 100 from the uniform-image generating unit 35. Furthermore, the clipping processing unit 36a reads a clipping coefficient K from the coefficient storage unit 36b. The clipping coefficient K is set in advance as a reference signal value to be compared with a signal value of each picture signal of the uniform image in the clipping process, and stored in the coefficient storage unit 36b. The clipping processing unit 36a performs a process of comparing the acquired picture signals of respective pixels of the uniform image (in particular, the R picture signals) with the clipping coefficient K one by one with control by the control unit 38, and subsequently performs the clipping process on each picture signal of the uniform image based on a result of the comparison process. In the clipping process, among R picture signal values of respective pixels of the uniform image being a processing target, the clipping processing unit 36a replaces an R picture signal value larger than the clipping coefficient K with a signal value equal to the clipping coefficient K, and maintains an R picture signal value equal to or smaller than the clipping coefficient K as the R picture signal value of the uniform image. The clipping processing unit 36a sends each picture signal of the uniform image obtained by the clipping process to the offset processing unit 36c.

Among the pixels of the uniform image described above, a pixel having the R picture signal value larger than the clipping coefficient K may be a pixel that has received light normally reflected by the observed region 100. When the pixel has received the normal reflected light, a luminance value of the pixel becomes extremely larger than those of neighboring pixels. If the pixel that has received the normal reflected light is contained in the uniform image, a picture signal value of the fluorescence image divided by a picture signal value (luminance value) of the pixel that has received the normal light in the uniform image becomes extremely small in the standardization process performed on the fluorescence image by the standardization processing unit 36e, which will be described later. This may disturb visibility of the whole fluorescence image obtained by the standardization process. To prevent the disturbance, the clipping processing unit 36a performs the clipping process on each picture signal of the uniform image as described above to thereby reduce a luminance difference between the pixel that has received the normal reflected light and other pixels in the uniform image.

The offset processing unit 36c performs the offset process of uniformly adding a predetermined value to each picture signal of the uniform image described above. More specifically, the offset processing unit 36c acquires from the clipping processing unit 36a each picture signal of the uniform image obtained by the clipping process. The offset processing unit 36c uniformly adds a pre-set signal value to each picture signal of the uniform image obtained by the clipping process, with control by the control unit 38. Consequently, the offset processing unit 36c sets each R picture signal value of each pixel of the uniform image to a signal value larger than zero, thereby preventing a zero division process from being performed on the picture signal during the standardization process performed on the fluorescence image by the standardization processing unit 36e described later. The offset processing unit 36c sends each picture signal of the uniform image obtained by the offset process to the normalization processing unit 36d.

The normalization processing unit 36d performs the normalization process on each picture signal of the uniform image described above. More specifically, the normalization processing unit 36d acquires from the offset processing unit 36c each picture signal of the uniform image obtained by the offset process. The normalization processing unit 36d performs the normalization process to set a signal value of each picture signal of the uniform image obtained by the offset process to a value in a range larger than 0.0 and equal to or smaller than 1.0, with control by the control unit 38. In this case, the normalization processing unit 36d extracts a maximum signal value from among the R picture signal values of respective pixels of the uniform image obtained by the offset process, and divides the R picture signal values of respective pixels by the extracted maximum signal value. The normalization processing unit 36d sends each picture signal of the uniform image obtained by the normalization process to the standardization processing unit 36e.

The standardization processing unit 36e corrects each picture signal of the fluorescence image of the observed region 100 through the standardization process. More specifically, the standardization processing unit 36e acquires from the normalization processing unit 36d each picture signal of the uniform image obtained by the normalization process. The standardization processing unit 36e also acquires each picture signal of the fluorescence image of the observed region 100 stored in the fluorescence-image buffer 33 described above. The standardization processing unit 36e performs the standardization process on each picture signal of the fluorescence image of the observed region 100 acquired from the fluorescence-image buffer 33, based on the uniform image obtained by the normalization process, with control by the control unit 38. In this case, the standardization processing unit 36e divides the picture signal of the fluorescence image of the observed region 100 by the picture signal of the uniform image obtained by the normalization process (in particular, by the R picture signal), and performs the standardization process on luminance of respective pixels of the fluorescence image, for each identical pixel between the uniform image obtained by the normalization process and the fluorescence image of the observed region 100. Through the standardization process, the standardization processing unit 36e performs the correction process of each picture signal of the fluorescence image of the observed region 100, and generates a standardized fluorescence image based on each picture signal obtained by the correction process. The standardized fluorescence image is a fluorescence image obtained by the correction process by the standardization processing unit 36e, and thus the lightness and darkness of the fluorescence that vary depending on the imaging distance between the observed region 100 as an object and the fluorescence imaging unit 28 is corrected. The standardization processing unit 36e sends each picture signal of the standardized fluorescence image of the observed region 100 to the colorization processing unit 36f.

The colorization processing unit 36f performs the colorization process on the standardized fluorescence image corrected by the standardization process described above. More specifically, the colorization processing unit 36f acquires each picture signal of the standardized fluorescence image of the observed region 100 from the standardization processing unit 36e. The colorization processing unit 36f calculates pseudo color signals corresponding to respective picture signals of the acquired standardized fluorescence image for each pixel, and performs the colorization process on the standardized fluorescence image based on each acquired pseudo color signal, with control by the control unit 38. The colorization processing unit 36f sends each acquired picture signal of the standardized fluorescence image, i.e., each pseudo color signal of the standardized fluorescence image of the observed region 100 to the output unit 37.

Figure 10:
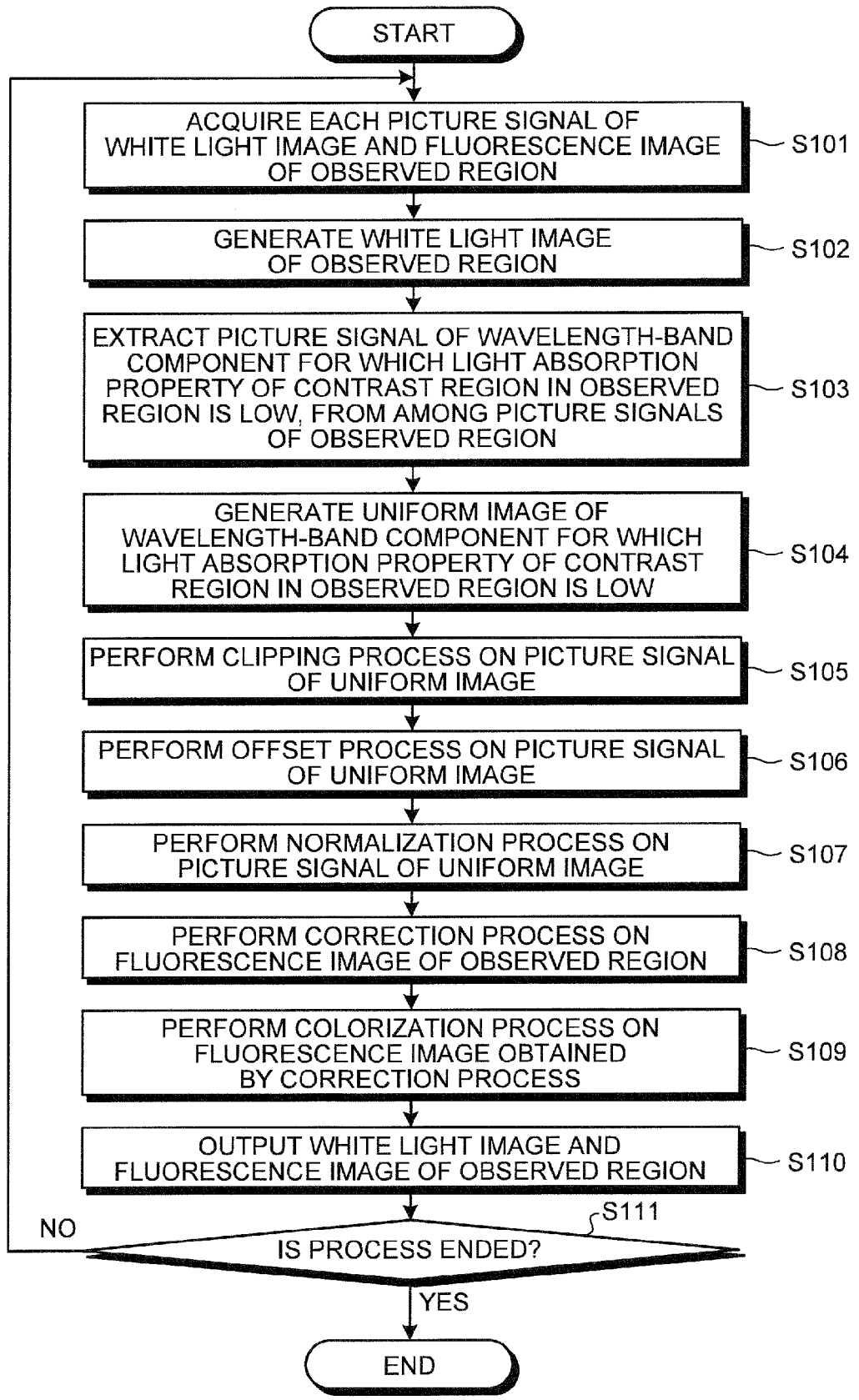
FIG. 10 is a flowchart illustrating an example of a process procedure performed by the image processing device according to the first embodiment.

Next, operations of the image processing device 30 according to the first embodiment of the present invention are described below. FIG. 10 is a flowchart illustrating an example of a process procedure performed by the image processing device according to the first embodiment of the present invention. The image processing device 30 of the first embodiment executes the process procedure illustrated in FIG. 10 to display on the image output device 50 the white light image of the observed region 100 and the standardized fluorescence image obtained by the colorization process.

Specifically, as illustrated in FIG. 10, the image processing device 30 acquires each picture signal of the white light image and the fluorescence image of the observed region 100 (Step S101). At Step S101, the control unit 38 controls the A/D converting unit 31 to digitalize a picture signal of the single-chip imaging element, which is acquired by the white-light imaging unit 26 when the observed region 100 is irradiated with white light, and digitalize a picture signal of the single-chip imaging element, which is acquired by the fluorescence imaging unit 28 when the observed region 100 is irradiated with excitation light. When the observed region 100 is irradiated with the white light, the A/D converting unit 31 sequentially acquires B picture signals, G picture signals, and R picture signals of single-chip imaging element from the white-light imaging unit 26, digitalizes the B picture signals, G picture signals, and R picture signals of single-chip imaging element acquired from the white-light imaging unit 26, and sends the digitalized picture signals to the white-light-image buffer 32, with the control by the control unit 38. In contrast, when the observed region 100 is irradiated with the excitation light, the A/D converting unit 31 sequentially acquires picture signals of single-chip imaging element from the fluorescence imaging unit 28, digitalizes the picture signals of the single-chip imaging element acquired from the fluorescence imaging unit 28, and sends the digitalized picture signals to the fluorescence-image buffer 33, with the control by the control unit 38.

The image processing device 30 then generates a white light image of the observed region 100 captured by the white-light imaging unit 26 at Step S101 (Step S102). At Step S102, the control unit 38 controls the white-light-image generating unit 34 to generate the white light image based on each B picture signal, each G picture signal, and each R picture signal of the single-chip imaging element acquired from the white-light imaging unit 26. With the control by the control unit 38, the white-light-image generating unit 34 reads the digitalized B picture signals, G picture signals, and R picture signals of the single-chip imaging element from the white-light-image buffer 32, and generates the white light image of the observed region 100 based on the read B picture signals, G picture signals, and R picture signals of the single-chip imaging element.

Subsequently, the image processing device 30 extracts a picture signal of the wavelength-band component for which the light absorption property of the contrast region of the observed region 100 is low, from among the picture signals of the observed region 100 acquired from the white-light imaging unit 26 at Step S101 (Step S103). At Step S103, the control unit 38 controls the signal extracting unit 35a to extract the picture signal in the wavelength band for which the light absorptance of the contrast region of the observed region 100 is relatively low, from among the B picture signals, G picture signals, and R picture signals of the single-chip imaging element acquired from the white-light imaging unit 26. With the control by the control unit 38, the signal extracting unit 35a reads the digitalized B picture signals, G picture signals, and R picture signals of the single-chip imaging element from the white-light-image buffer 32. Then, the signal extracting unit 35a extracts each picture signal (each R picture signal for example) corresponding to the specific color filter described above from among the read B picture signals, G picture signals, and R picture signals of the single-chip imaging element.

The image processing device 30 then generates a uniform image of the wavelength-band component for which the light absorptance of the contrast region of the observed region 100 is low, based on the picture signals of the single-chip imaging element extracted at Step S103 (Step S104). At Step S104, the control unit 38 controls the interpolation processing unit 35c to generate the uniform image by performing the interpolation process of each picture signal in the specific wavelength band extracted by the signal extracting unit 35a. The interpolation processing unit 35c reads from the buffer 35b each picture signal of the single-chip imaging element corresponding to the specific color filter in the color filter group 25 described above, with the control by the control unit 38. Subsequently, the interpolation processing unit 35c performs the interpolation process of the read picture signals of the single-chip imaging element, and generates the uniform image of the wavelength-band component (a red component for example) corresponding to the specific color filter.

Subsequently, the image processing device 30 performs the clipping process on each picture signal of the uniform image generated at Step S104 (Step S105). At Step S105, the control unit 38 controls the clipping processing unit 36a to perform the clipping process on each picture signal of the uniform image generated by the interpolation processing unit 35c. With the control by the control unit 38, the clipping processing unit 36a performs a process of comparison between a signal value (a luminance value for example) of each picture signal of the single-chip imaging element, which is acquired from the interpolation processing unit 35c, and the clipping coefficient K, which is read from the coefficient storage unit 36b. Based on a result of the process of comparison, the clipping processing unit 36a replaces a picture signal value larger than the clipping coefficient K with a signal value equal to the clipping coefficient K, and maintains a picture signal value equal to or smaller than the clipping coefficient K as a picture signal value of the uniform image.

The image processing device 30 then performs the offset process on each picture signal of the uniform image obtained by the clipping process at Step S105 (Step S106). At Step S106, the control unit 38 controls the offset processing unit 36c to perform the offset process on each picture signal of the uniform image obtained by the clipping process. With the control by the control unit 38, the offset processing unit 36c acquires from the clipping processing unit 36a each picture signal of the single-chip imaging element obtained by the clipping process, and uniformly adds a predetermined signal value to the signal value of each acquired picture signal of the single-chip imaging element.

Subsequently, the image processing device 30 performs the normalization process on each picture signal of the uniform image obtained by the offset process at Step S106 (Step S107). At Step S107, the control unit 38 controls the normalization processing unit 36d to perform the normalization process on each picture signal of the uniform image obtained by the offset process. With the control by the control unit 38, the normalization processing unit 36d acquires from the offset processing unit 36c each picture signal of the single-chip imaging element obtained by the offset process, extracts a maximum signal value from among the signal values of respective acquired picture signals of the single-chip imaging element, and divides the signal value of each picture signal by the extracted maximum signal value. Consequently, the signal value of each picture signal of the single-chip imaging element obtained by the offset process becomes a value in a range larger than 0.0 and equal to or smaller than 1.0.

The image processing device 30 then performs the correction process on the fluorescence image of the observed region 100 based on each picture signal of the uniform image obtained by the normalization process at Step S107 (Step S108). At Step S108, the control unit 38 controls the standardization processing unit 36e to correct each picture signal of the fluorescence image of the observed region 100 through the standardization process. With the control by the control unit 38, the standardization processing unit 36e acquires from the normalization processing unit 36d each picture signal of the single-chip imaging element obtained by the normalized process, and reads from the fluorescence-image buffer 33 each picture signal of the single-chip imaging element corresponding to the fluorescence image of the observed region 100. Subsequently, the standardization processing unit 36e divides a signal value of each picture signal of the single-chip imaging element obtained from the fluorescence-image buffer 33 by the signal value of each picture signal of the single-chip imaging element obtained from the normalization processing unit 36d. In this case, the standardization processing unit 36e performs a division process on the signal value of the picture signal for each identical pixel between the two images. The standardization processing unit 36e performs the standardization process on the luminance of each pixel of the fluorescence image of the observed region 100 as described above and thereby performs the correction process of each picture signal of the fluorescence image of the observed region 100. Consequently, the standardization processing unit 36e generates a standardized fluorescence image based on each picture signal obtained by the correction process.

The image processing device 30 then performs the colorization process on the fluorescence image of the observed region 100 obtained by the correction process at Step S108 (Step S109). At Step S109, the control unit 38 controls the colorization processing unit 36f to perform the colorization process on the standardized fluorescence image of the observed region 100 generated by the standardization processing unit 36e. With the control by the control unit 38, the colorization processing unit 36f acquires from the standardization processing unit 36e each picture signal of the single-chip imaging element corresponding to the standardized fluorescence image, and calculates the pseudo color signal for each pixel based on the signal intensity of each acquired picture signal of the single-chip imaging element. The colorization processing unit 36f performs the colorization process on the standardized fluorescence image based on each pseudo color signal calculated for each pixel as described above.

Subsequently, the image processing device 30 performs an output process of displaying the white light image and the fluorescence image of the observed region 100 onto the image output device 50 (Step S110). At Step S110, the control unit 38 controls the output unit 37 to output the white light image generated at Step S102 and the standardized fluorescence image obtained by the colorization process at Step S109 onto the image output device 50. With the control by the control unit 38, the output unit 37 acquires each picture signal corresponding to the three-chip imaging elements from the white-light-image generating unit 34 and also acquires each pseudo color signal of the standardized fluorescence image from the colorization processing unit 36f. The output unit 37 outputs each picture signal corresponding to the three-chip imaging elements acquired from the white-light-image generating unit 34 to the image output device 50. Consequently, the white light image of the observed region 100 based on each picture signal corresponding to the three-chip imaging elements is displayed onto the image output device 50. Furthermore, the output unit 37 outputs each pseudo color signal of the standardized fluorescence image to the image output device 50. Consequently, the standardized fluorescence image of the observed region 100 based on each pseudo color signal is displayed in color onto the image output device 50.

At Step S110, the image output device 50 is allowed to display the white light image of the observed region 100 and the standardized fluorescence image obtained by the colorization process side by side in the same screen, or to display the images by superimposing them one on top of the other.

After the process procedure at Step S110 described above is completed, and when a predetermined process-end operation, such as off operation, is performed (YES at Step S111), the image processing device 30 ends the process. In this case, the control unit 38 receives instruction information to end the process from the input device 40, and ends the operations of each component of the image processing device 30 based on the received instruction information. In contrast, when the process-end operation is not performed (NO at Step S110), the image processing device 30 returns the process to Step S101 described above, and repeats the process procedure from Step S101. In this case, the control unit 38 executes the process procedure from Step S101 to Step S111 described above, and controls each component of the image processing device 30 appropriately.

Figure 11:
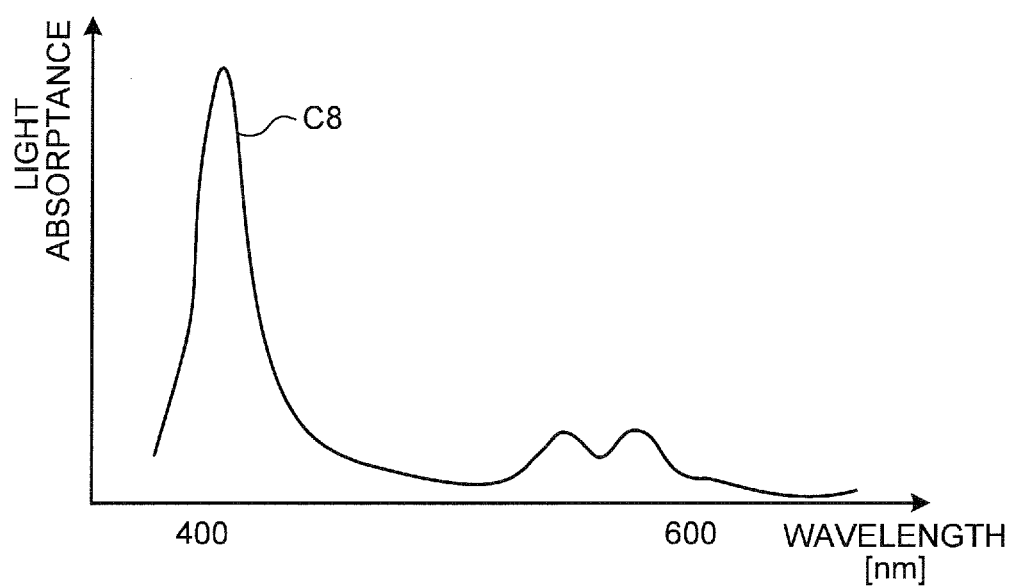
FIG. 11 is a schematic diagram illustrating an example of a light absorption property of a blood vessel being a contrast region in an observed region.
Figure 12:
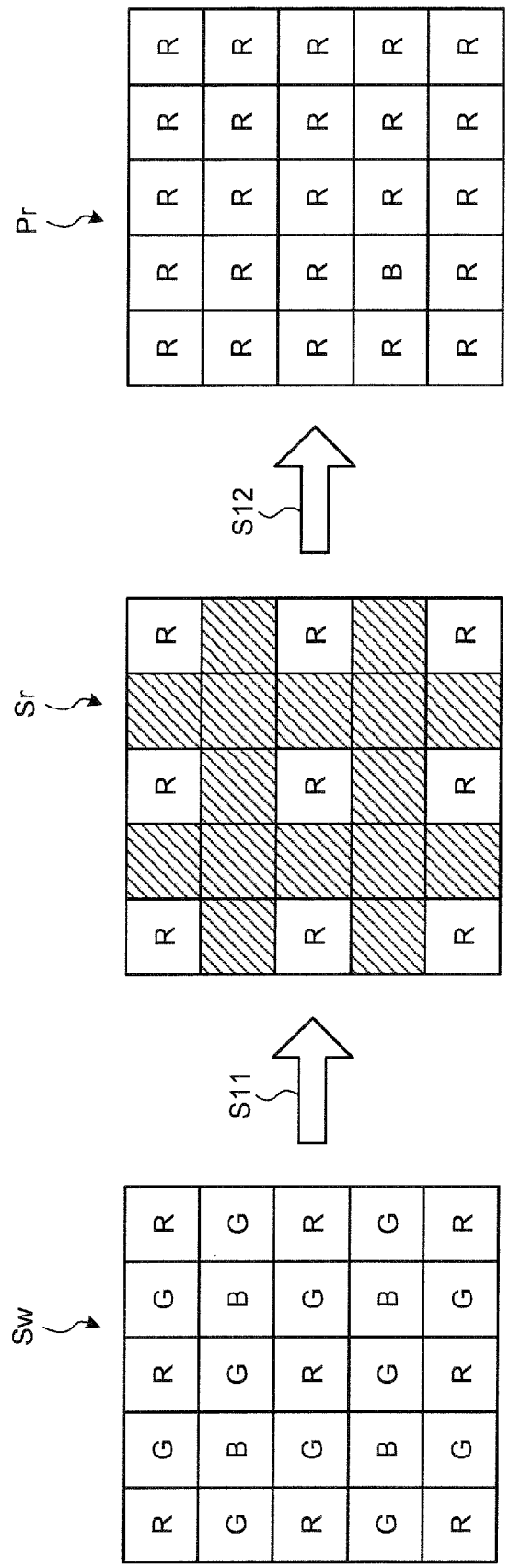
FIG. 12 is a schematic diagram explaining how to generate a uniform image of a red component for which the light absorption property of the blood vessel being the contrast region is low.
Figure 13:
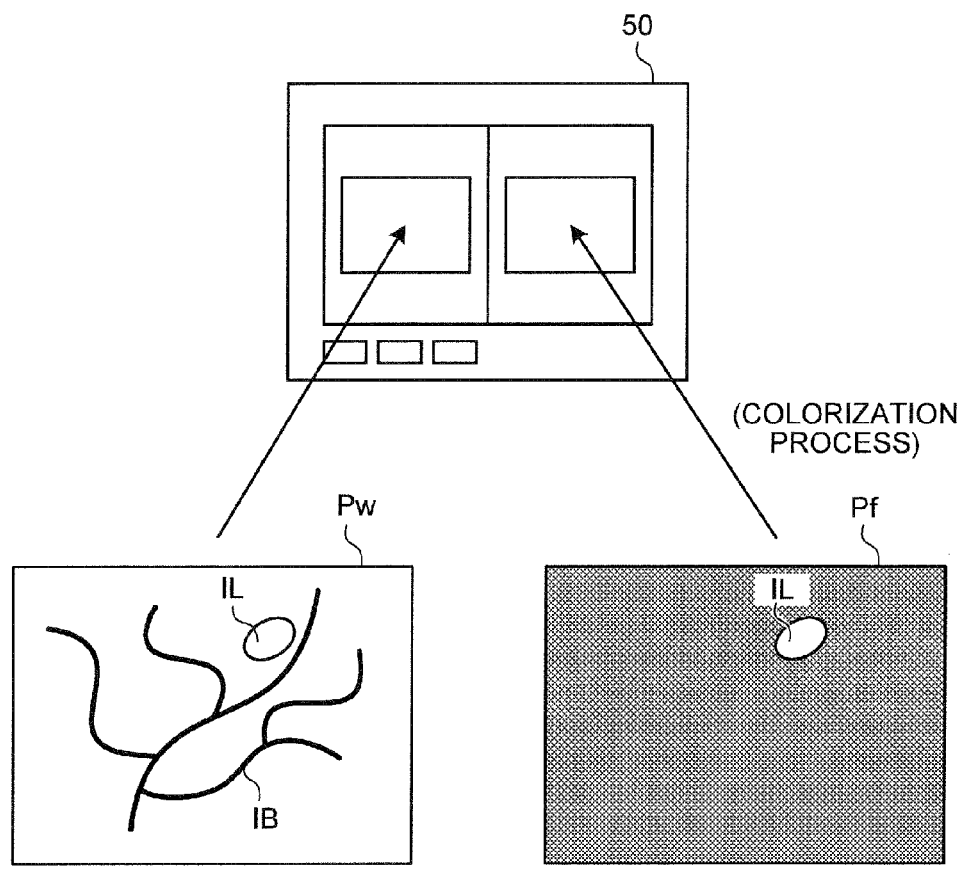
FIG. 13 is a schematic diagram illustrating how a white light image and a standardized fluorescence image of the observed region are displayed in color on an image output device according to the first embodiment.
Figure 14:
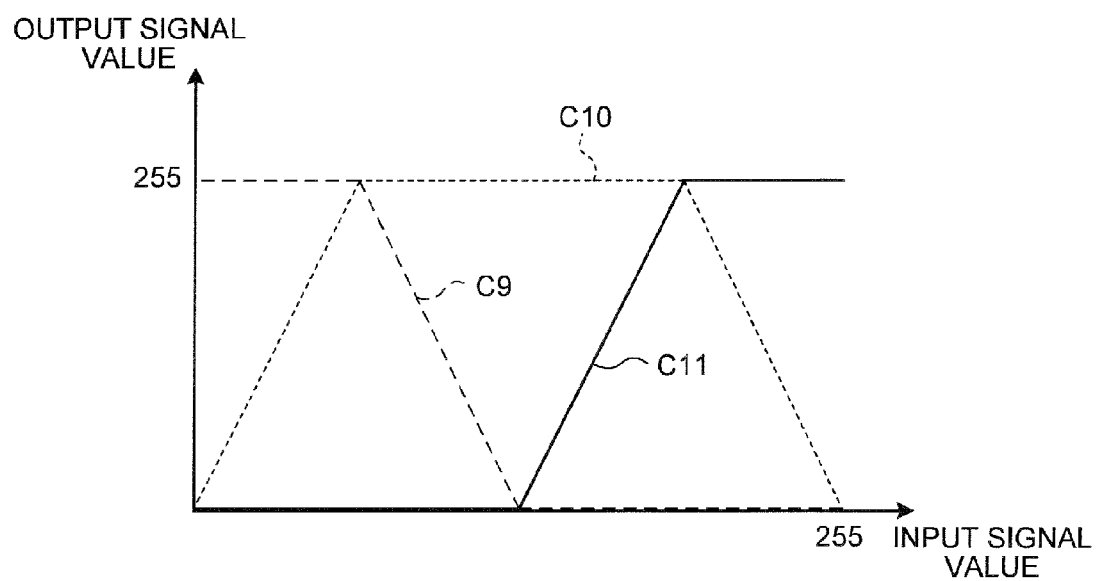
FIG. 14 is a schematic diagram illustrating an example of a tone curve used for a colorization process performed on the standardized fluorescence image according to the first embodiment.

Next, operations of the uniform-image generating unit 35 and the correction processing unit 36 of the above-mentioned image processing device 30 are described in detail below with an example in which the contrast region present in the observed region 100 of the endoscope apparatus 1 according to the first embodiment of the present invention is a blood vessel. FIG. 11 is a schematic diagram illustrating an example of the light absorption property of the blood vessel being the contrast region in the observed region. FIG. 12 is a schematic diagram explaining how to generate a uniform image of the red component for which the light absorption property of the blood vessel being the contrast region is low. FIG. 13 is a schematic diagram illustrating how the white light image and the standardized fluorescence image of the observed region are displayed in color on the image output device. FIG. 14 is a schematic diagram illustrating an example of a tone curve used for the colorization process performed on the standardized fluorescence image.

When the contrast region in the observed region 100 is a blood vessel, the uniform-image generating unit 35 generates a uniform image of a wavelength-band component for which the light absorption property of the blood vessel is relatively low, at Steps S103 and S104 illustrated in FIG. 10.

More specifically, the signal extracting unit 35a reads from the white-light-image buffer 32 each B picture signal, each G picture signal, and each R picture signal of the single-chip imaging element corresponding to a pixel array of the white light image of the observed region 100. Subsequently, as illustrated in FIG. 12, the signal extracting unit 35a extracts, from a picture signal group Sw as an assembly of each B picture signal, each G picture signal, and each R picture signal of the single-chip imaging element, each R picture signal corresponding to the specific color filter in the color filter group 25 described above, i.e., the red light filter that transmits light in a wavelength band for which the light absorption property of the blood vessel is low. Consequently, the signal extracting unit 35a obtains an R picture signal group Sr. In FIG. 12, the picture signal group Sw and the R picture signal group Sr are connected by an arrow S11.

The interpolation processing unit 35c reads from the buffer 35b each R picture signal of the single-chip imaging element extracted by the signal extracting unit 35a. The interpolation processing unit 35c performs the interpolation process of each read R picture signal of the single-chip imaging element. Accordingly, the interpolation processing unit 35c allocates the R picture signals to respective spaces (see portions indicated by diagonal lines in FIG. 12) of the B picture signals and the G picture signals, which have been thinned out during the process of extracting each R picture signal by the signal extracting unit 35a as described above. As a result, as illustrated in FIG. 12, the interpolation processing unit 35c generates a uniform image Pr of a picture signal of one frame based on the wavelength-band component, which corresponds to the red light filter being the specific color filter when the blood vessel appears as the contrast region, i.e., the uniform image of the red component. In FIG. 12, the R picture signal group Sr and the uniform image Pr are connected by an arrow S12.

Due to hemoglobin in the blood vessel, the blood vessel being the contrast region in the observed region 100 has light absorption property as indicated by a correlation line C8 of wavelength versus light absorptance illustrated in FIG. 11, in which a peak appears in a wavelength band near 400 nm and light absorptance is relatively decreased in a wavelength band equal to or longer than 600 nm. In other words, the blood vessel in the observed region 100 can hardly absorb light in a wavelength band of 600 nm or longer, e.g., red light of 600 nm to 680 nm extracted from the white light by the red light filter in the color filter group 25 described above. In this case, the signal extracting unit 35a extracts each R picture signal in a wavelength band of 600 nm to 680 nm for example from the picture signal group Sw of the single-chip imaging element described above, and the interpolation processing unit 35c generates the uniform image Pr of the red component of 600 nm to 680 nm by performing the interpolation process of each R picture signal extracted by the signal extracting unit 35a. As a result, the interpolation processing unit 35c is able to prevent occurrence of the edge, which is a pixel portion having luminance largely different from that of neighboring pixels due to the blood vessel, in the observed region 100, and generate the uniform image Pr having low contrast and accurately reflecting light illuminance distribution.

Meanwhile, when the contrast region in the observed region 100 is a blood vessel, the correction processing unit 36 performs the correction process on each picture signal of the fluorescence image of the observed region 100 based on the uniform image Pr of the red component, and subsequently performs the colorization process on the standardized fluorescence image being the fluorescence image obtained by the correction process, at Steps S108 and S109 illustrated in FIG. 10.

More specifically, the standardization processing unit 36e reads from the fluorescence-image buffer 33 each picture signal of the single-chip imaging element corresponding to the pixel array of the fluorescence image of the observed region 100, and acquires from the normalization processing unit 36d each R picture signal of the uniform image Pr of the red component describe above. Each R picture signal of the uniform image Pr has been subjected to the clipping process by the clipping processing unit 36a, the offset process by the offset processing unit 36c, and the normalization process by the normalization processing unit 36d in the process procedure from Steps S105 to S107 of FIG. 10. The standardization processing unit 36e divides the signal value (the luminance value for example) of the picture signal of the single-chip imaging element corresponding to the fluorescence image by the signal value of the R picture signal (the luminance value for example) of the uniform image Pr, for each corresponding pixel between the fluorescence image of the observed region 100 and the uniform image Pr. Consequently, the standardization processing unit 36e performs the correction process of each picture signal of the single-chip imaging element corresponding to the fluorescence image, and generates the standardized fluorescence image of the observed region 100 based on each picture signal obtained by the correction process.

Each R picture signal of the uniform image Pr used for the correction process performed on the fluorescence image by the standardization processing unit 36e has been subjected to the clipping process by the clipping processing unit 36a. Therefore, the standardization processing unit 36e is able to perform the correction process on each picture signal of the fluorescence image of the observed region 100 by each R picture signal of the uniform image Pr, in which a luminance difference between a pixel that has received the normal reflected light and a pixel that has received reflected light other than the normal reflected light is reduced. Consequently, the standardization processing unit 36e is able to correct each picture signal of the fluorescence image with high accuracy without being affected by the normal reflected light from the observed region 100.

Furthermore, each R picture signal of the uniform image Pr used for the correction process performed on the fluorescence image by the standardization processing unit 36e has been subjected to the offset process by the offset processing unit 36c. Therefore, the standardization processing unit 36e is able to divide the signal value of each picture signal of the fluorescence image by the signal value of each R picture signal of the uniform image Pr without performing the zero division process on the picture signals during the standardization process performed on the fluorescence image of the observed region 100.

Moreover, each R picture signal of the uniform image Pr used for the correction process performed on the fluorescence image by the standardization processing unit 36e has been subjected to the normalization process by the normalization processing unit 36d. In other words, the signal value of each R picture signal of the uniform image Pr obtained by the normalization process is in a range larger than 0.0 and equal to or smaller than 1.0. The standardization processing unit 36e divides the signal value of each picture signal of the fluorescence image by the signal value of each R picture signal of the uniform image Pr obtained by the normalization process, so that a luminance value of a pixel corresponding to a fluorescence generated portion present at a relatively short imaging distance can be maintained and a luminance value of a pixel corresponding to a fluorescence generated portion present at a relatively long imaging distance can be emphasized. Consequently, the standardization processing unit 36e is able to correct the lightness and darkness of the fluorescence that vary depending on the imaging distance between the observed region 100 as an object and the fluorescence imaging unit 28. As a result, it is possible to emphasize the luminance value of a pixel corresponding to the fluorescence generated portion regardless of the imaging distance.

Meanwhile, as illustrated in FIG. 13, a standardized fluorescence image Pf of the observed region 100 generated by the standardization processing unit 36e described above is displayed on the image output device 50 after the colorization process. The colorization processing unit 36f acquires each picture signal of the standardized fluorescence image Pf of the observed region 100 from the standardization processing unit 36e, and calculates the pseudo color signal for each pixel according to the intensity of the acquired picture signal of the standardized fluorescence image Pf. In this case, the colorization processing unit 36f performs a pseudo color signal calculation process on the standardized fluorescence image Pf based on tone curves C9 to C11 of picture signals of respective color components as illustrated in FIG. 14. More specifically, in FIG. 14, the tone curve C9 is a tone curve corresponding to the B picture signal being a blue component, the tone curve C10 is a tone curve corresponding to the G picture signal being a green component, and the tone curve C11 is a tone curve corresponding to the R picture signal being the red component. The colorization processing unit 36f calculates each output signal value of the B picture signal, the G picture signal, and the R picture signal corresponding to input signal values of the picture signals of the standardized fluorescence image Pf based on the tone curves C9 to C11 of respective color components. Subsequently, the colorization processing unit 36f calculates the pseudo color signals corresponding to the picture signals of the standardized fluorescence image Pf by combining the calculated output signal values of respective color components with one another. The colorization processing unit 36f performs a process of calculating the pseudo color signal for each pixel of the standardized fluorescence image Pf.

Each pseudo color signal of the standardized fluorescence image Pf obtained by the colorization processing unit 36f is transmitted to the image output device 50 via the output unit 37 described above. The image output device 50 displays the standardized fluorescence image Pf of the observed region 100 in color based on each pseudo color signal acquired from the output unit 37. As described above, the standardized fluorescence image Pf is a fluorescence image in which each picture signal is corrected based on the uniform image Pr, which has low contrast and accurately reflects the light illuminance distribution because occurrence of the edge caused by the contrast region such as the blood vessel is prevented. The lightness and darkness of the fluorescence caused by variation in the imaging distance between the observed region 100 and the fluorescence imaging unit 28 is corrected with high accuracy in the standardized fluorescence image Pf without being affected by the edge caused by the contrast region such as the blood vessel. The image output device 50 displays an image IL of the affected area 101, which is present inside the observed region 100, over a pseudo color image of the standardized fluorescence image Pf, by using pixels having relatively high luminance regardless of the imaging distance between the observed region 100 and the fluorescence imaging unit 28.

The image output device 50 is able to separately acquire each picture signal of a white light image Pw of the observed region 100 from the output unit 37 described above, and, as illustrated in FIG. 13 for example, display the white light image Pw of the observed region 100 and the pseudo color image of the standardized fluorescence image Pf in color and side-by-side on the same screen. With the image output device 50, a user such as a doctor or a nurse can observe the white light image Pw of the observed region 100 and the pseudo color image of the standardized fluorescence image Pf simultaneously. A reference symbol "IB" in FIG. 13 indicates an image of the blood vessel.

As described above, according to the first embodiment of the present invention, each picture signal of the normal light image, which is based on normal light received from the observed region via the color filter group formed of the filters having different spectral characteristics, and each picture signal of the fluorescence image, which is based on fluorescence generated from the observed region irradiated with excitation light, are acquired. Subsequently, each picture signal corresponding to the specific color filter, which is contained in the color filter group and transmits light in a wavelength band for which the light absorption property of the contrast region of the observed region is low, is extracted from among the picture signals of the normal light image. Then, the uniform image of the wavelength-band component corresponding to the specific color filter is generated based on the extracted picture signals. Subsequently, each picture signal of the fluorescence image of the observed region is corrected based on each picture signal of the generated uniform image. Therefore, additional components are not necessary, i.e., a light source that is able to apply light in a wavelength band for which the light absorption property of the contrast region of the observed region is low, or a processing circuit that performs a low-pass filter processing on the picture signals used for the correction process performed on the fluorescence image are not necessary. Furthermore, it is possible to prevent occurrence of the edge caused by the contrast region in the observed region, and easily generate the uniform image having low contrast and accurately reflecting the light illuminance distribution, based on the picture signals in the wavelength band corresponding to the specific color filter in the existing color filter group. With use of the picture signals of the uniform image having low contrast, it is possible to accurately correct the luminance of the fluorescence image being an observation target with simple structure and without being affected by the edge caused by the contrast region such as the blood vessel. As a result, it is possible to easily acquire a high-quality fluorescence image in which the lightness and darkness of the fluorescence caused by variation in the imaging distance to the observed region is corrected with high accuracy.

Furthermore, according to the first embodiment, among the picture signal values of the uniform image, a picture signal value larger than a predetermined reference signal value is replaced with the reference signal value by the clipping process. Therefore, it is possible to reduce a luminance difference between a pixel that has received normal reflected light and a pixel that has received reflected light other than the normal reflected light in the uniform image. With use of each picture signal of the uniform image obtained by the clipping process, each picture signal of the fluorescence image can be corrected with high accuracy and without being affected by the normal reflected light from the observed region.

Moreover, according to the first embodiment, each picture signal of the uniform image is set to a signal value larger than zero by the offset process. Therefore, in the standardization process on the fluorescence image of the observed region, it is possible to divide the signal value of each picture signal of the fluorescence image by the signal value of each picture signal of the uniform image without performing the zero division process on the picture signals.

Furthermore, according to the first embodiment, each picture signal value of the uniform image is set to a signal value in a range larger than 0.0 and equal to or smaller than 1.0 by the normalization process. Therefore, it is possible to maintain a luminance value of a pixel corresponding to the fluorescence generated portion present at a relatively short imaging distance, and emphasize a luminance value of a pixel corresponding to the fluorescence generated portion present at a relatively long imaging distance. Consequently, it is possible to correct the lightness and darkness of the fluorescence that vary depending on the imaging distance. As a result, it is possible to emphasize the luminance value of the pixel corresponding to the fluorescence generated portion regardless of the imaging distance.

Second Embodiment

A second embodiment of the present invention will be described. In the first embodiment described above, the uniform image is generated based on the R picture signals corresponding to the red light filter in the color filter group 25, as the image information for correcting the fluorescence image of the observed region 100. However, in the second embodiment, a uniform image is generated based on a picture signal of an infrared component (hereinafter, referred to as "IR picture signal") corresponding to an infrared light filter in a color filter group arranged on a light receiving portion of a white-light imaging unit.

Figure 15:
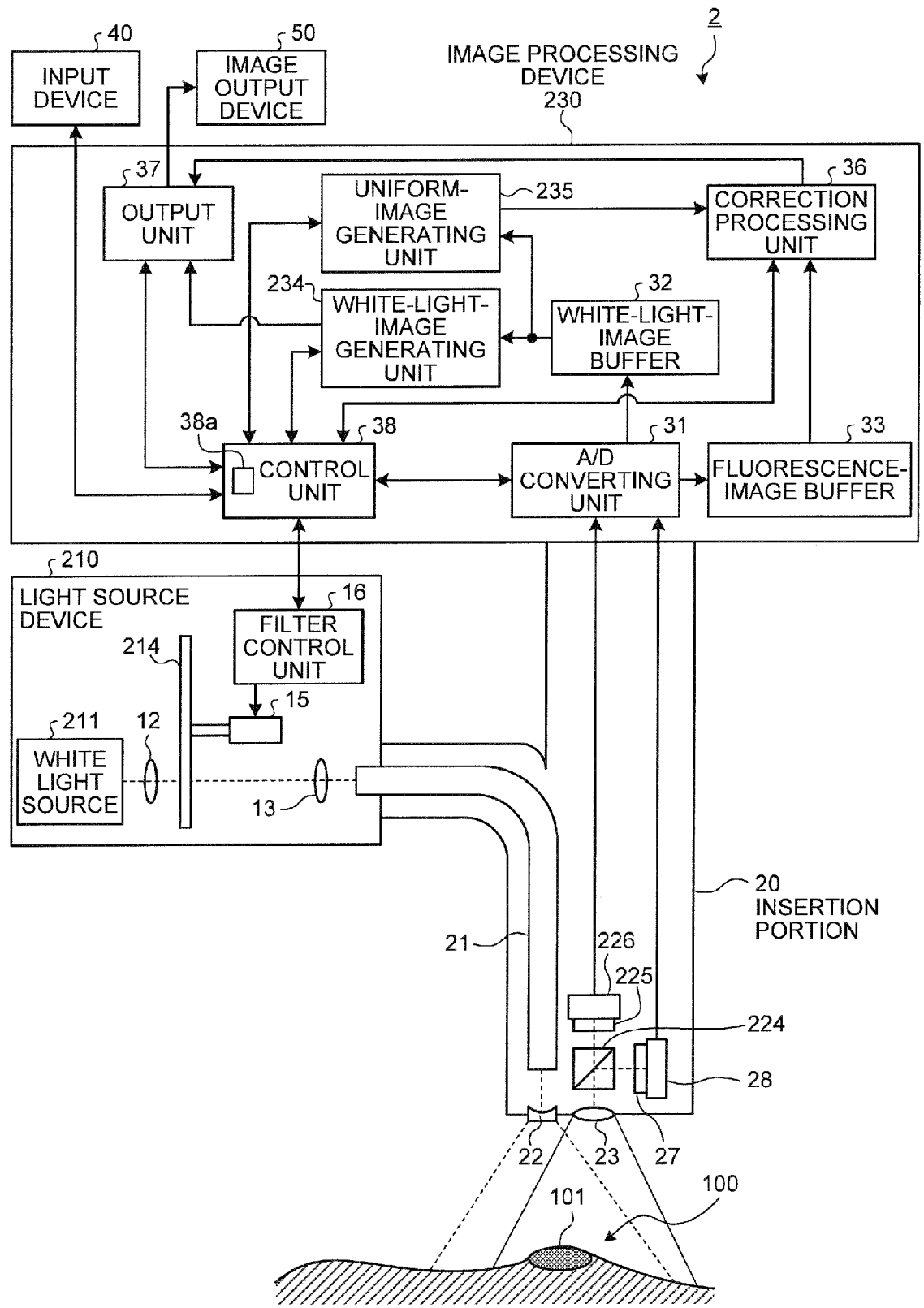
FIG. 15 is a block diagram schematically showing a configuration example of an endoscope apparatus according to a second embodiment of the present invention.

FIG. 15 is a block diagram schematically showing a configuration example of an endoscope apparatus according to the second embodiment of the present invention. As illustrated in FIG. 15, an endoscope apparatus 2 according to the second embodiment includes a light source device 210 instead of the light source device 10 of the endoscope apparatus 1 of the first embodiment, and a half mirror 224 instead of the dichroic mirror 24. The endoscope apparatus 2 also includes a color filter group 225 with four colors (infrared, red, green, and blue) instead of the color filter group 25 with three colors (red, green, and blue), a white-light imaging unit 226, which is able to receive infrared light, instead of the white-light imaging unit 26, and an image processing device 230 instead of the image processing device 30. The light source device 210 includes a white light source 211 instead of the white light source 11 of the first embodiment described above, and a rotary filter 214 instead of the rotary filter 14. The image processing device 230 includes a white-light-image generating unit 234 instead of the white-light-image generating unit 34 of the image processing device 30 of the first embodiment, and a uniform-image generating unit 235 instead of the uniform-image generating unit 35. The other configurations of the endoscope apparatus 2 are the same as those of the first embodiment, and the same components are denoted by the same symbols.

The light source device 210 includes the white light source 211 and the rotary filter 214 as described above, and functions as a light source unit that switchably applies white light, which is in a wide band including a wavelength band of infrared light, and excitation light, which excites a fluorescent agent, to the observed region 100. The light source device 210 has the same functions as those of the light source device 10 of the first embodiment described above except for functions of the white light source 211 and the rotary filter 214.

The white light source 211 is realized with use of a light source that is able to emit white light in a wide band including at least a wavelength band of infrared light, and emits white light in the wide band (in a wavelength band of 300 nm to 800 nm for example) according to operation of a switch (not shown) of the light source device 210. The white light emitted from the white light source 211 contains blue light, green light, red light, and infrared light.

Figure 16:
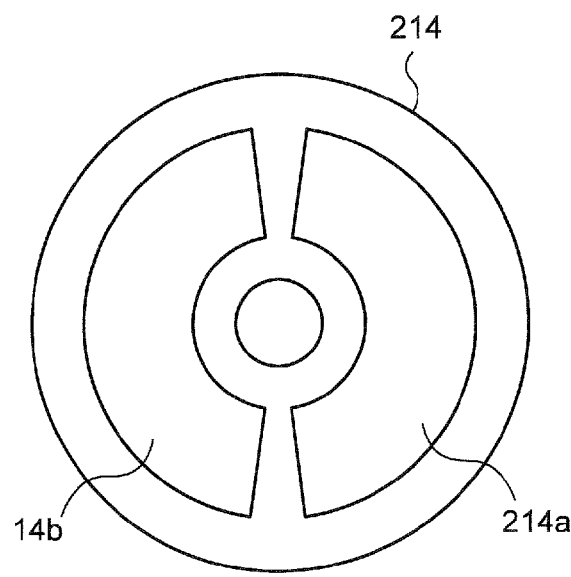
FIG. 16 is a schematic diagram illustrating a configuration example of a rotary filter according to the second embodiment.
Figure 17:
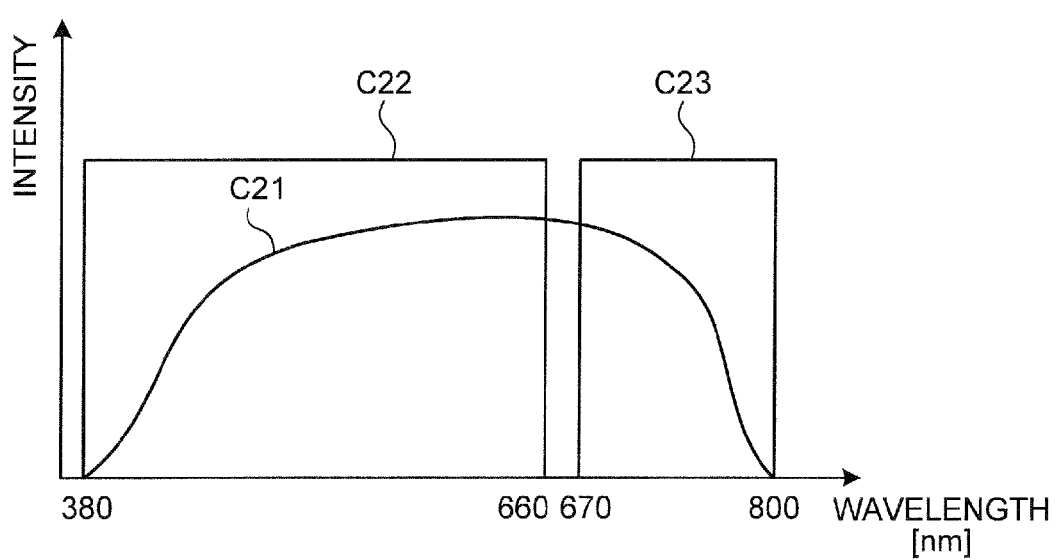
FIG. 17 is a schematic diagram illustrating an example of a spectral characteristic of a white light filter included in the rotary filter according to the second embodiment.
Figure 18:
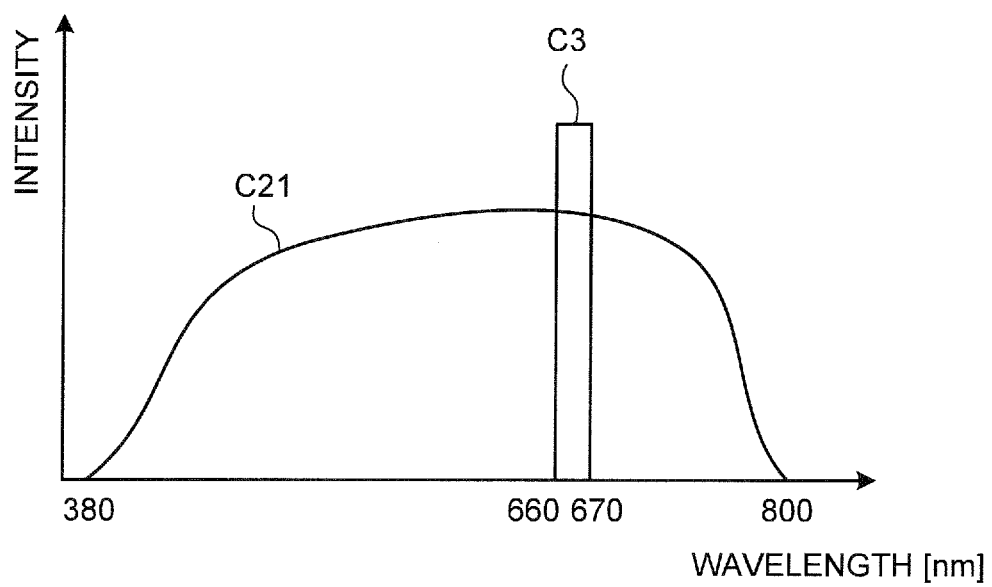
FIG. 18 is a schematic diagram illustrating an example of a spectral characteristic of an excitation light filter included in the rotary filter according to the second embodiment.

The rotary filter 214 extracts light in a predetermined wavelength band from the white light emitted from the white light source 211. FIG. 16 is a schematic diagram illustrating a configuration example of the rotary filter according to the second embodiment. FIG. 17 is a schematic diagram illustrating an example of a spectral characteristic of a white light filter included in the rotary filter according to the second embodiment. FIG. 18 is a schematic diagram illustrating an example of a spectral characteristic of an excitation light filter included in the rotary filter according to the second embodiment. In FIGS. 17 and 18, a correlation line C21 of wavelength versus intensity is illustrated as an example of the spectral characteristic of the white light emitted from the white light source 211. As illustrated in FIG. 16, the rotary filter 214 includes a white light filter 214a having an excitation-light cutting function, instead of the white light filter 14a of the first embodiment described above. The rotary filter 214 also includes the excitation light filter 14b identical to that of the first embodiment.

The white light filter 214a transmits white light in a wavelength band other than that of excitation light, from the white light in the wide band emitted from the white light source 211. More specifically, the white light filter 214a has spectral transmittance to transmit light in a wavelength band other than a wavelength band of 660 nm to 670 nm within a wavelength band of 380 nm to 800 nm, as indicated by correlation lines C22 and C23 of wavelength versus intensity illustrated in FIG. 17. In other words, the white light filter 214a has the spectral transmittance to transmit light in the wavelength bands of 380 nm to 660 nm and 670 nm to 800 nm. The white light filter 214a having such spectral transmittance removes excitation light being light in the wavelength band of 660 nm to 670 nm and extracts white light in the wavelength band other than that of the excitation light, from the white light having the spectral characteristic indicated by the correlation line C21 of wavelength versus intensity illustrated in FIG. 17. The white light extracted by the white light filter 214a contains a blue component, a green component, a red component, and an infrared component. The white light filter 214a transmits the white light containing the infrared component and the like as normal light to be applied to the observed region 100. A spectral characteristic of the white light transmitted through the white light filter 214a is calculated by multiplying the spectral characteristic of the white light from the white light source 211 (see the correlation line C21) by the spectral transmittance of the white light filter 214a (see the correlation lines C22 and C23).

In the rotary filter 214, the excitation light filter 14b transmits excitation light in the wavelength band of 660 nm to 670 nm from the white light in the wide band emitted from the white light source 211, similarly to the first embodiment. A spectral characteristic of the excitation light transmitted through the excitation light filter 14b is calculated by multiplying the spectral characteristic of the white light from the white light source 211 (see the correlation line C21) by the spectral transmittance of the excitation light filter 14b (see the correlation line C3).

The rotary filter 214 having the white light filter 214a and the excitation light filter 14b as described above rotates in a circumferential direction with drive of the motor 15 similarly to the first embodiment. Accordingly, the white light filter 214a and the excitation light filter 14b are switchably put in the optical path of the white light from the white light source 211 (see a dashed line in the light source device 210 illustrated in FIG. 15). The rotary filter 214 transmits the white light except for the excitation light and containing the infrared light when the white light filter 214a is put in the optical path, and transmits the excitation light similar to that described in the first embodiment when the excitation light filter 14b is put in the optical path. In other words, the rotary filter 214 alternately transmits the white light, which contains the infrared light, and the excitation light.

The white light, which contains the infrared light, and the excitation light alternately emitted from the light source device 210 are alternately applied to the observed region 100 via the light guide fiber 21, similarly to the first embodiment.

The half mirror 224 equally separates the light coming from the observed region 100 and transmitted through the objective lens 23 toward the white-light imaging unit 226 side and the fluorescence imaging unit 28 side. More specifically, when the observed region 100 is irradiated with the white light containing the infrared light, the half mirror 224 separates the white light, which contains the infrared light and is reflected by the observed region 100, towards an optical path on the white-light imaging unit 226 side and an optical path on the fluorescence imaging unit 28 side. In contrast, when the observed region 100 is irradiated with the excitation light, the half mirror 224 separates fluorescence generated from the observed region 100 and the excitation light reflected by the observed region 100 toward the optical path on the white-light imaging unit 226 side and the optical path on the fluorescence imaging unit 28 side.

Figure 19:
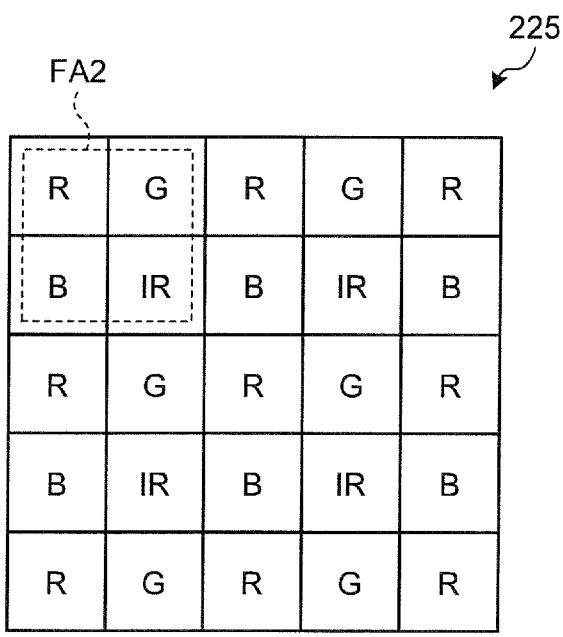
FIG. 19 is a schematic diagram illustrating a configuration example of a color filter group arranged on a light receiving surface of a white-light imaging unit according to the second embodiment.
Figure 20:
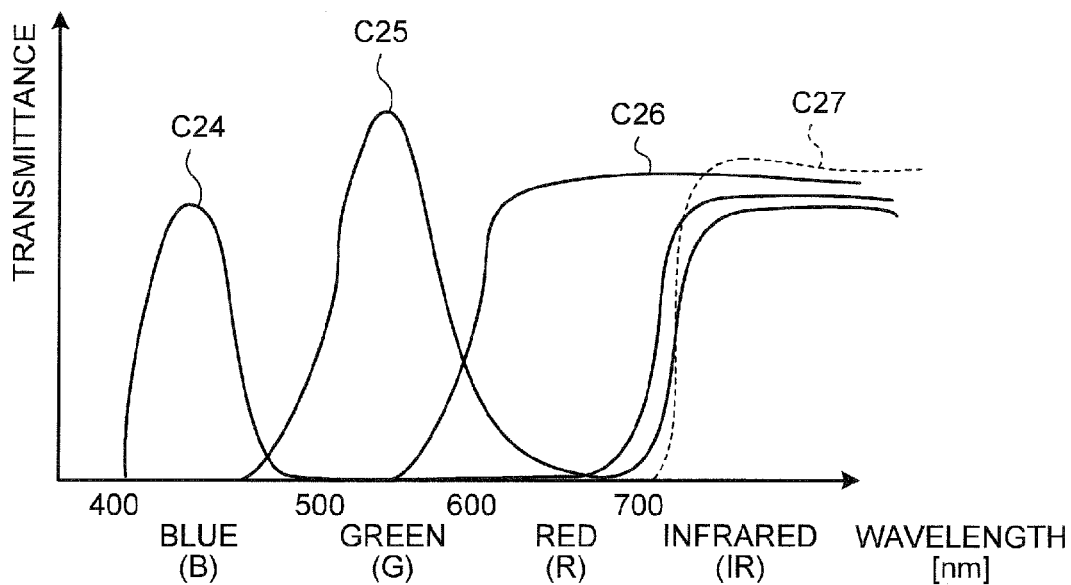
FIG. 20 is a schematic diagram illustrating an example of transmittance properties of the color filter group according to the second embodiment.

The color filter group 225 includes a plurality of four types of color filters having different spectral characteristics. The color filter group 225 splits the white light from the observed region 100 into light of each wavelength component for each pixel of the white-light imaging unit 226, and transmits the light of each wavelength component toward each pixel of the white-light imaging unit 226. FIG. 19 is a schematic diagram illustrating a configuration example of the color filter group arranged on a light receiving surface of the white-light imaging unit according to the second embodiment. FIG. 20 is a schematic diagram illustrating an example of transmittance properties of the color filter group according to the second embodiment. The color filter group 225 is a primary color filter in the form of mosaic containing a plurality of red light filters (R) being color filters that transmit red light, a plurality of green light filters (G) being color filters that transmit green light, a plurality of blue light filters (B) being color filters that transmit blue light, and a plurality of infrared light filters (IR) being color filters that transmit infrared light. Furthermore, the color filter group 225 is formed with use of a color filter assembly FA2 of 2×2 as a base unit, and at least one red light filter, one green light filter, one blue light filter, and one infrared light filter are contained in the base unit.

In the color filter group 225, the blue light filters have spectral transmittance to transmit blue light in a wavelength band of 400 nm to 500 nm and infrared light in a wavelength band of 700 nm or longer as indicated by a correlation line C24 of wavelength versus transmittance illustrated in FIG. 20. The green light filters have spectral transmittance to transmit green light in a wavelength band of 480 nm to 600 nm and infrared light in a wavelength band of 700 nm or longer as indicated by a correlation line C25 of wavelength versus transmittance illustrated in FIG. 20. The red light filters have spectral transmittance to transmit red light in a wavelength band of 580 nm to 700 nm and infrared light in a wavelength band of 700 nm or longer as indicated by a correlation line C26 of wavelength versus transmittance illustrated in FIG. 20. The infrared light filters have spectral transmittance to transmit infrared light in a wavelength band of 700 nm or longer as indicated by a correlation line C27 of wavelength versus transmittance illustrated in FIG. 20.

In the color filter group 225, a 50%-transmission band of the blue light filters is from 430 nm to 480 nm, a 50%-transmission band of the green light filters is from 510 nm to 580 nm, and a 50%-transmission band of the red light filters is from 600 nm to 680 nm. In contrast, the spectral transmittance property of the infrared light filter indicated by the correlation line C27 of FIG. 20 for example is defined based on the spectral transmittance property of the blue light filter indicated by the correlation line C24 for example, the spectral transmittance property of the green light filter indicated by the correlation line C25 for example, and the spectral transmittance property of the red light filter indicated by the correlation line C26 for example. In other words, a start wavelength at which the spectral transmittance of the infrared light filter starts increasing is set on the longest wavelength side (e.g., 700 nm) of each wavelength band of the blue light, the green light, and the red light, and an optical filter having the spectral transmittance property with spectral transmittance increased from the set start wavelength is used as the infrared light filter in the color filter group 225.

The color filter group 225 structured as described above extracts, from the white light coming from the observed region 100 and separated toward the optical path on the white-light imaging unit 226 side by the half mirror 224, blue light of 430 nm to 480 nm for example and infrared light by the blue light filters, green light of 510 nm to 580 nm for example and infrared light by the green light filters, red light of 600 nm to 680 nm for example and infrared light by the red light filters, and infrared light of 700 nm or longer for example by the infrared light filters. Each blue light filter in the color filter group 225 transmits a blue component and an infrared component of the white light toward each blue pixel of the white-light imaging unit 226. Each green light filter in the color filter group 225 transmits a green component and the infrared component of the white light toward each green pixel of the white-light imaging unit 226. Each red light filter in the color filter group 225 transmits a red component and the infrared component of the white light toward each red pixel of the white-light imaging unit 226. Each infrared light filter in the color filter group 225 transmits the infrared component of the white light toward each pixel corresponding to the infrared component, i.e., each infrared pixel of the white-light imaging unit 226.

The color filter group 225 may be others as long as the color filter assembly FA2 of 2×2 is used as the base unit and at least one red light filter (R), one green light filter (G), one blue light filter (B), and one infrared light filter (IR) are contained in the base unit as described above. Accordingly, the size of the color filter group 225 is not limited by 5×5 as illustrated in FIG. 19. In other words, the color filter group 225 may be formed in a desired size with a desired number of color filters containing at least the infrared light filter, depending on the light receiving surface of the white-light imaging unit 226.

The white-light imaging unit 226 is realized with use of a Bayer-type color imaging element in which color filters having different spectral characteristics are arranged on pixels in the light receiving element. More specifically, the white-light imaging unit 226 does not include an infrared-light cut filter, and includes the color filter group 225 described above on the light receiving surface. A light receiving portion of the white-light imaging unit 226 is formed with use of a pixel assembly of 2×2 for example as a base unit, and is constructed of a pixel group containing a plurality of pixel assemblies each being the base unit, similarly to the white-light imaging unit 26 of the first embodiment. In the light receiving portion of the white-light imaging unit 226, the color filter assembly FA2 as the base unit of the color filter group 225 described above is arranged for each pixel assembly being the base unit. In other words, the red light filter, the green light filter, the blue light filter, and the infrared light filter in the color filter assembly FA2 being the base unit of the color filter group 225 are provided on the pixel assembly being the base unit of the white-light imaging unit 226.

The white-light imaging unit 226 structured as described above receives, via the above-mentioned color filter group 225 for example, normal light coming from the observed region 100 and separated toward the optical path on the white-light imaging unit 226 side by the half mirror 224, i.e., white light (containing infrared light) reflected by the observed region 100 when the white light is applied from the light source device 10 to the observed region 100. Accordingly, the white-light imaging unit 226 captures a white light image being a color image of the observed region 100. In this case, the white-light imaging unit 226 causes each pixel in the pixel group to perform a photoelectric conversion process of normal light of each wavelength-band component (the blue component, the green component, the red component, and the infrared component) split from the white light by the color filter group 225 and generate a picture signal of each wavelength-band component corresponding to the white light image of the observed region 100.

The pixel group in the light receiving portion of the white-light imaging unit 226 is formed of a plurality of blue pixels on which the blue light filters of the color filter group 225 are arranged, a plurality of green pixels on which the green light filters of the color filter group 225 are arranged. Furthermore, the pixel group in the light receiving portion of the white-light imaging unit 226 includes a plurality of red pixels being pixels on which the red light filters of the color filter group 225 are arranged, and a plurality of infrared pixels being pixels on which the infrared light filters of the color filter group 225 are arranged. In the pixel group of the white-light imaging unit 226, the blue pixels receive normal light of a blue component (in a wavelength band of 430 nm to 480 nm for example) and infrared light in a wavelength of 700 nm or longer for example transmitted through the blue light filters from the white light coming from the observed region 100. The blue pixels perform the photoelectric conversion process on the received normal light of the blue component and the infrared light to thereby generate B picture signals of the observed region 100, i.e., B picture signals of the blue component containing the infrared component. The green pixels receive normal light of a green component (in a wavelength band of 510 nm to 580 nm for example) and the infrared light transmitted through the green light filters from the white light coming from the observed region 100. The green pixels perform the photoelectric conversion process on the received normal light of the green component and the infrared light to thereby generate G picture signals of the observed region 100, i.e., G picture signals of the green component containing the infrared component. The red pixels receive normal light of a red component (in a wavelength band of 600 nm to 680 nm for example) and the infrared light transmitted through the red light filters from the white light coming from the observed region 100. The red pixels perform the photoelectric conversion process of the received normal light of the red component and the infrared light to thereby generate R picture signals of the observed region 100, i.e., R picture signals of the red component containing the infrared component. The infrared pixels receive the infrared light transmitted through the infrared light filters from the white light coming from the observed region 100. The infrared pixels perform the photoelectric conversion process of the received infrared light to thereby generate IR picture signals being picture signals of the infrared component of the observed region 100. The white-light imaging unit 226 sequentially transmits to the A/D converting unit 31 of the image processing device 230 each B picture signal, each G picture signal, each R picture signal, and each IR picture signal constituting the white light image of the observed region 100 every time the white-light imaging unit 226 captures the white light image of the observed region 100.

When the excitation light is applied to the observed region 100 by the light source device 210, the white-light imaging unit 226 receives light coming from the observed region 100 and separated toward the optical path on the white-light imaging unit 226 side by the half mirror 224, i.e., fluorescence emitted from the observed region 100 and excitation light reflected by the observed region 100, via the color filter group 225. In this case, similarly to each picture signal of the white light image, the white-light imaging unit 226 performs the photoelectric conversion process on the excitation light and the fluorescence received from the observed region 100, and generates each picture signal of the excitation light and the fluorescence. Subsequently, the white-light imaging unit 226 sequentially transmits each generated picture signal of the excitation light and the fluorescence to the A/D converting unit 31 of the image processing device 230. However, each picture signal of the excitation light and the fluorescence generated by the white-light imaging unit 226 is deleted by the A/D converting unit 31 with the control by the control unit 38 of the image processing device 230. In other words, from among the picture signals generated by the white-light imaging unit 226, each B picture signal, each G picture signal, each R picture signal, and each IR picture signal corresponding to the white light image obtained when the white light is applied to the observed region 100 are stored in the white-light-image buffer 32 after the A/D converting unit 31 completes the digital conversion process.

On the other hand, in the second embodiment, the barrier filter 27 blocks the white light (containing the infrared light) reflected by the observed region 100 and the excitation light, and transmits the fluorescence from the observed region 100 from the light, which is coming from the observed region 100 and separated toward the optical path on the fluorescence imaging unit 28 side by the half mirror 224. Due to the action of the barrier filter 27, similarly to the first embodiment, the fluorescence imaging unit 28 receives the fluorescence emitted from the observed region 100 and transmitted through the barrier filter 27. As described above, the fluorescence imaging unit 28 sequentially transmits each picture signal of the fluorescence image of the observed region 100 to the image processing device 230 every time the fluorescence imaging unit 28 captures the fluorescence image of the observed region 100.

The image processing device 230 includes, as described above, the white-light-image generating unit 234 instead of the white-light-image generating unit 34 of the image processing device 30 of the first embodiment, and the uniform-image generating unit 235 instead of the uniform-image generating unit 35. The image processing device 230 causes the white-light-image generating unit 234 to generate the white light image of the observed region 100 based on B picture signals, G picture signals, and R picture signals, each containing the infrared component as described above. Furthermore, the image processing device 230 causes the uniform-image generating unit 235 to generate the uniform image based on the IR picture signal described above. The image processing device 230 has the same functions as those of the image processing device 30 of the first embodiment described above except for the functions of the white-light-image generating unit 234 and the uniform-image generating unit 235.

In the image processing device 230, the A/D converting unit 31 digitalizes, from among the picture signals of the observed region 100 acquired from the white-light imaging unit 226 described above, each B picture signal, each G picture signal, each R picture signal, and each IR picture signal corresponding to the white light image obtained when the observed region 100 is irradiated with the white light. Subsequently, the A/D converting unit 31 sequentially transmits the digitalized picture signals to the white-light-image buffer 32. The white-light-image buffer 32 temporarily stores therein the digitalized B picture signals, G picture signals, R picture signals, and IR picture signals obtained from the A/D converting unit 31, and then appropriately transmits the digitalized B picture signals, G picture signals, R picture signals, and IR picture signals to the white-light-image generating unit 234 and the uniform-image generating unit 235.

The white-light-image generating unit 234 generates the white light image of the observed region 100 based on each picture signal of one frame temporarily stored in the white-light-image buffer 32. More specifically, the white-light-image generating unit 234 acquires, from the white-light-image buffer 32, each B picture signal, each G picture signal, each R picture signal, and each IR picture signal of the single-chip imaging element corresponding to the white light image of one frame. The white-light-image generating unit 234 performs an infrared-component removal process to remove the infrared component from each picture signal of the single-chip imaging element acquired from the white-light-image buffer 32, and generates the white light image of the observed region 100 based on each B picture signal, each G picture signal, and each R picture signal obtained by the infrared-component removal process. The white-light-image generating unit 234 sequentially performs the above-mentioned processes to generate the white light image of the observed region 100 frame by frame every time the white-light-image generating unit 234 acquires each picture signal of the white light image of one frame from the white-light-image buffer 32. The white-light-image generating unit 234 sequentially transmits each picture signal of the white light image of the observed region 100 generated as described above to the output unit 37.

Figure 21:
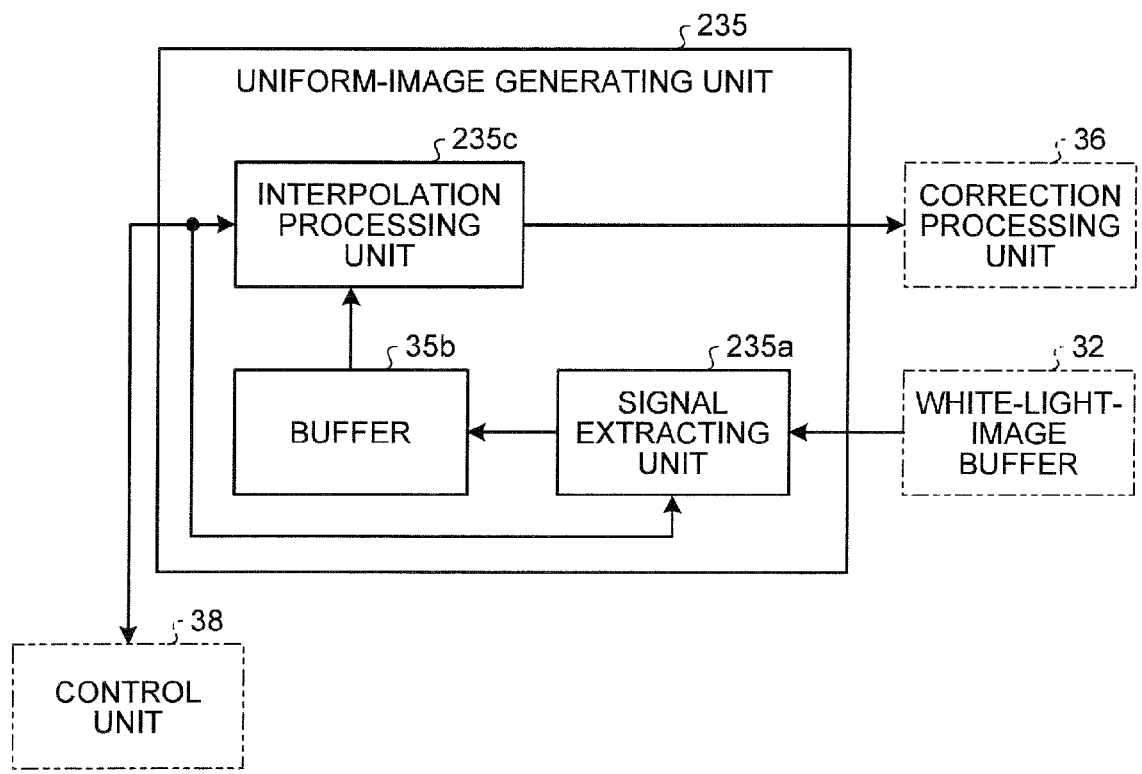
FIG. 21 is a block diagram schematically showing a configuration example of a uniform-image generating unit of an image processing device according to the second embodiment.

The uniform-image generating unit 235 generates a uniform image of the infrared component based on the IR picture signal from the white-light imaging unit 226, as a uniform image used for the correction process of correcting each picture signal of the fluorescence image of the observed region 100 captured by the fluorescence imaging unit 28 described above. FIG. 21 is a block diagram schematically showing a configuration example of the uniform-image generating unit of the image processing device according to the second embodiment. As illustrated in FIG. 21, the uniform-image generating unit 235 includes a signal extracting unit 235a instead of the signal extracting unit 35a of the uniform-image generating unit 35 of the first embodiment described above, and an interpolation processing unit 235c instead of the interpolation processing unit 35c. The other configurations of the uniform-image generating unit 235 are the same as those of the uniform-image generating unit 35 of the first embodiment (see FIG. 8), and the same components are denoted by the same symbols.

The signal extracting unit 235a extracts each picture signal corresponding to a specific color filter contained in the color filter group 225 of the white-light imaging unit 226 described above, from among the picture signals of the white light image stored in the white-light-image buffer 32, with control by the control unit 38. More specifically, the signal extracting unit 235a extracts each IR picture signal corresponding to the infrared light filter of the color filter group 225 from among each B picture signal, each G picture signal, each R picture signal, and each IR picture signal of one frame corresponding to the white light image of the observed region 100.

Among the blue light filter, the green light filter, the red light filter, and the infrared light filter, the infrared light filter is described as an example of the specific color filter that transmits light in a wavelength band for which a light absorption property of the contrast region (e.g., a blood vessel) present in the observed region 100 such as a body tissue is comparatively low. Furthermore, the infrared light filter transmits light (i.e., infrared light) at which the light absorption property of the contrast region such as the blood vessel becomes low compared with use of the red light filter being the specific color filter of the first embodiment described above. The signal extracting unit 235a extracts each IR picture signal corresponding to the infrared light filter being the specific color filter of the second embodiment, from among each B picture signal, each G picture signal, each R picture signal, and each IR picture signal of the single-chip imaging element acquired from the white-light-image buffer 32. In this case, the signal extracting unit 235a performs a process of thinning out each B picture signal corresponding to the blue light filters in the color filter group 225, each G picture signal corresponding to the green light filters in the color filter group 225, and each R picture signal corresponding to the red light filters in the color filter group 225. The signal extracting unit 235a sequentially transmits each IR picture signal of the single-chip imaging element extracted as described above to the buffer 35b, with control by the control unit 38.

The interpolation processing unit 235c performs the interpolation process of each picture signal in the specific wavelength band extracted by the signal extracting unit 235a, and generates a uniform image of a wavelength-band component corresponding to the specific color filter in the color filter group 225 described above. More specifically, the interpolation processing unit 235c acquires from the buffer 35b each IR picture signal of the single-chip imaging element, which is a picture signal in the specific wavelength band extracted by the signal extracting unit 235a, and performs the interpolation process of each acquired IR picture signal of the single-chip imaging element, with control by the control unit 38. By performing the interpolation process of each IR picture signal, the interpolation processing unit 235c allocates the IR picture signals to respective spaces of the B picture signals, the G picture signals, and the R picture signals which have been thinned out during the process of extracting each IR picture signal by the signal extracting unit 235a as described above. Consequently, the interpolation processing unit 235c generates the uniform image of a picture signal of one frame based on the wavelength-band component corresponding to the infrared light filter being the specific color filter described above, i.e., the uniform image of the infrared component being the wavelength-band component corresponding to the infrared light filter. The interpolation processing unit 235c sequentially sends each picture signal (in particular, each IR picture signal) of the generated uniform image to the correction processing unit 36, with control by the control unit 38.

In the second embodiment, the correction processing unit 36 performs the correction process of each picture signal of the fluorescence image of the observed region 100 by using each IR picture signal of the uniform image of the infrared component from the interpolation processing unit 235c, instead of use of the uniform image of the red component based on each R picture signal as described earlier. The correction process performed on the fluorescence image by the correction processing unit 36 is the same as that described in the first embodiment except for use of each IR picture signal of the uniform image of the infrared component as described above.

Figure 22:
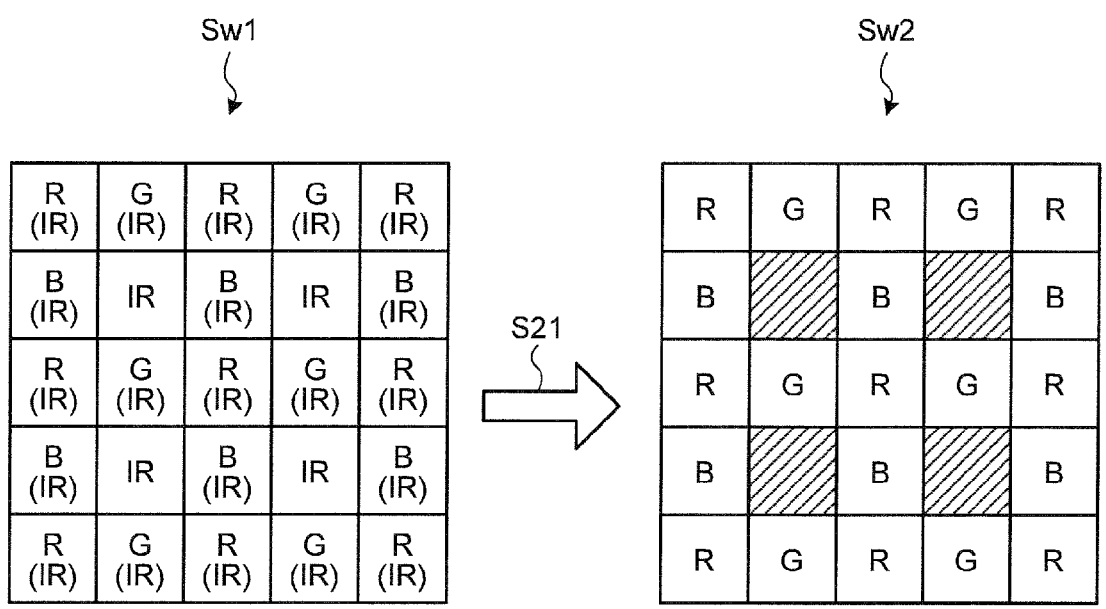
FIG. 22 is a schematic diagram explaining an infrared-component removal process according to the second embodiment, which is performed when a white light image of an observed region is generated.
Figure 23:
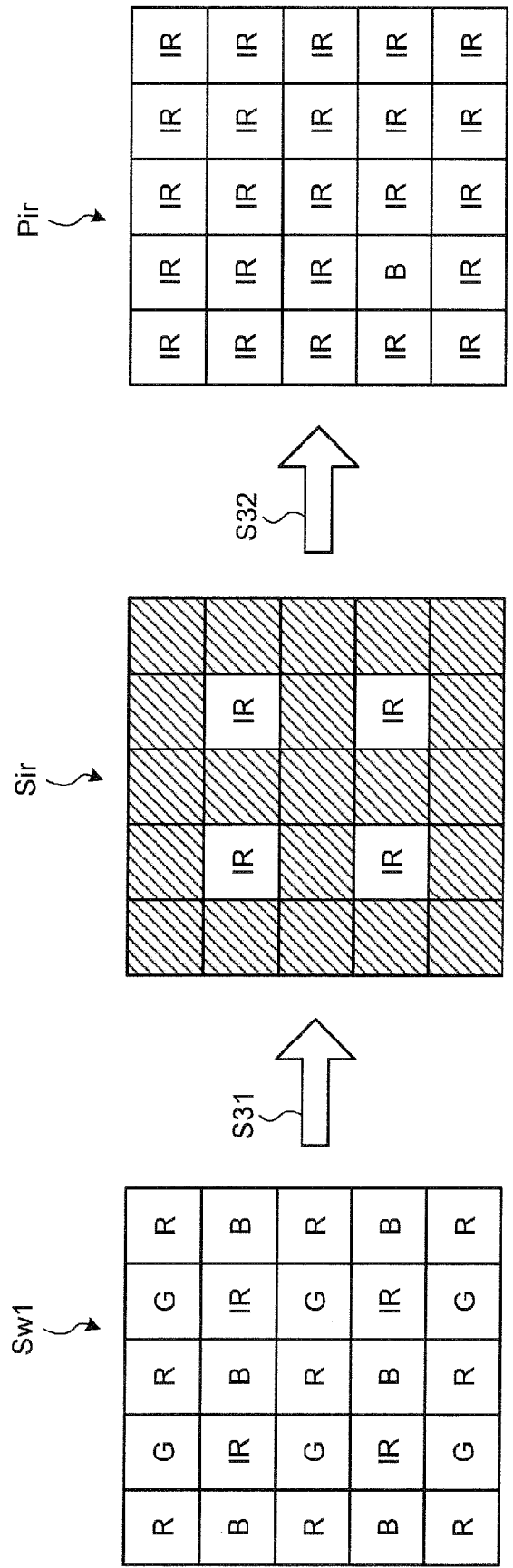
FIG. 23 is a schematic diagram explaining how to generate a uniform image of an infrared component for which a light absorption property of a blood vessel being a contrast region is low according to the second embodiment.

Next, operations of the image processing device 230 according to the second embodiment of the present invention are described in detail below. FIG. 22 is a schematic diagram explaining the infrared-component removal process according to the second embodiment, which is performed when the white light image of the observed region is generated. FIG. 23 is a schematic diagram explaining how to generate the uniform image of the infrared component for which a light absorption property of a blood vessel being the contrast region is low according to the second embodiment. The image processing device 230 of the second embodiment operates in the same manner as the image processing device 30 of the first embodiment described above except for operations of generating the white light image of the observed region 100 and generating the uniform image. In other words, the image processing device 230 executes the process procedure substantially the same as that from Steps S101 to S111 of FIG. 10. In this case, the image processing device 230 performs different processes from those of the first embodiment described above in the process procedure from Steps S102 to S104 in the process procedure from Steps S101 to S111.

At Step S102 described above, the image processing device 230 generates the white light image of the observed region 100 by removing the infrared component from each B picture signal, each G picture signal, and each R picture signal containing the infrared component. More specifically, the white-light-image generating unit 234 reads from the white-light-image buffer 32 each B picture signal, each G picture signal, each R picture signal, and each IR picture signal of the single-chip imaging element corresponding to the pixel array of the white light image of the observed region 100. Each B picture signal, each G picture signal, and each R picture signal of the single-chip imaging element contain the infrared components as described above. As illustrated in FIG. 22, the white-light-image generating unit 234 performs the infrared-component removal process on a picture signal group Sw1, which is an assembly of each B picture signal, each G picture signal, each R picture signal, and each IR picture signal of the single-chip imaging element, so that the infrared component, which is the wavelength-band component unnecessary for color expression of the white light image of the observed region 100, is removed from the picture signal group Sw1. As a result, a picture signal group Sw2 is generated. In FIG. 22, the picture signal group Sw1 and the picture signal group Sw2 are connected by an arrow S21.

More specifically, in the infrared-component removal process performed on the picture signal group Sw1, the white-light-image generating unit 234 calculates a ratio between the spectral transmittance in an infrared region of the blue light filter and the spectral transmittance of the infrared light filter (see FIG. 20) in the color filter group 225 described above, and subtracts a product of the calculated ratio and the signal value of the IR picture signal from the signal value of each B picture signal of the single-chip imaging element. Consequently, the white-light-image generating unit 234 removes the infrared component from each B picture signal of the single-chip imaging element. On the other hand, the white-light-image generating unit 234 calculates a ratio between the spectral transmittance in an infrared region of the green light filter and the spectral transmittance of the infrared light filter in the color filter group 225 described above, and subtracts a product of the calculated ratio and the signal value of the IR picture signal from each G picture signal of the single-chip imaging element. Consequently, the white-light-image generating unit 234 removes the infrared component from each G picture signal of the single-chip imaging element. Furthermore, the white-light-image generating unit 234 calculates a ratio between the spectral transmittance in an infrared region of the red light filter and the spectral transmittance of the infrared light filter in the color filter group 225 described above, and subtracts a product of the calculated ratio and the signal value of the IR picture signal from each R picture signal of the single-chip imaging element. Consequently, the white-light-image generating unit 234 removes the infrared component from each R picture signal of the single-chip imaging element. Moreover, the white-light-image generating unit 234 removes each IR picture signal of the single-chip imaging element from the picture signal group Sw1.

Subsequently, the white-light-image generating unit 234 performs the interpolation process of each picture signal in the picture signal group Sw2 obtained by the infrared-component removal process. Consequently, the white-light-image generating unit 234 calculates a color component of each infrared pixel (see portions indicated by diagonal lines in FIG. 22) corresponding to each IR picture signal, and generates a picture signal corresponding to the three-chip imaging elements, in which the color components contained in the pixel assembly being the base unit described above are combined with each other, per pixel assembly being the base unit. The white-light-image generating unit 234 performs a color conversion process, a tone conversion process, and the like on each picture signal corresponding to the three-chip imaging elements generated as described above to thereby generate the white light image of the observed region 100.

Meanwhile, at Steps S103 and S104 described above, the uniform-image generating unit 235 of the image processing device 230 extracts each IR picture signal corresponding to the infrared light filter that transmits infrared light being the wavelength-band component for which the light absorption property of the contrast region such as a blood vessel present in the observed region 100 is low, and generates the uniform image of the infrared component based on each extracted IR picture signal.

More specifically, at Step S103, the signal extracting unit 235a reads from the white-light-image buffer 32 each B picture signal, each G picture signal, each R picture signal, and each IR picture signal of the single-chip imaging element corresponding to the pixel array of the white light image of the observed region 100. Subsequently, as illustrated in FIG. 23, the signal extracting unit 235a extracts each IR picture signal corresponding to the infrared light filter being the specific color filter in the color filter group 225 described above, from the picture signal group Sw1 being the assembly of each B picture signal, each G picture signal, each R picture signal, and each IR picture signal of the single-chip imaging element, whereby an IR picture signal group Sir is obtained. The infrared light filter being the specific color filter transmits the infrared light in a wavelength band for which the light absorption property of the contrast region such as a blood vessel is low. In FIG. 23, the picture signal group Sw1 and the IR picture signal group Sir are connected by an arrow S31.

Then, at Step S104, the interpolation processing unit 235c reads from the buffer 35b each IR picture signal of the single-chip imaging element extracted by the signal extracting unit 235a. The interpolation processing unit 235c performs the interpolation process of each read picture signal of the single-chip imaging element to allocate the IR picture signals to respective spaces (see portions indicated by diagonal lines in FIG. 23) of the B picture signals, the G picture signals, and the R picture signals which have been thinned out during the process of extracting each IR picture signal by the signal extracting unit 235a described above. Consequently, as illustrated in FIG. 23, the interpolation processing unit 235c generates a picture signal of one frame of the wavelength-band component corresponding to the infrared light filter being the specific color filter of the second embodiment, i.e., a uniform image Pir of the infrared component. In FIG. 23, the IR picture signal group Sir and the uniform image Pir are connected by an arrow S32.

The blood vessel as an example of the contrast region in the observed region 100 has light absorption property as illustrated in FIG. 11, in which a peak appears in a wavelength band near 400 nm and light absorptance is relatively decreased in a wavelength band equal to or longer than 600 nm. In other words, the blood vessel in the observed region 100 can hardly absorb light in a wavelength band of 600 nm or longer. Furthermore, the blood vessel having such light absorption property is less able to absorb the infrared light in a wavelength band of 700 nm or longer extracted from the white light by the infrared light filter in the color filter group 225 than it is to the light in a wavelength band of 600 nm to 680 nm, i.e., the red light extracted from the white light by the red light filter in the color filter group 225. The signal extracting unit 235a extracts, from the picture signal group Sw1 of the single-chip imaging element described above, each IR picture signal in a wavelength band for which the light absorptance of the blood vessel is much lower. Then, the interpolation processing unit 235c performs the interpolation process of each IR picture signal to thereby generate the uniform image Pir of the infrared component. Consequently, the interpolation processing unit 235c can more easily suppress occurrence of the edge, which is a pixel portion having luminance largely different from that of a neighboring pixel in accordance with the blood vessel in the observed region 100, and generate the uniform image Pir having lower contrast and reflecting light illuminance distribution with increased accuracy.

As described above, according to the second embodiment, each picture signal containing the infrared component based on the normal light received from the observed region is acquired via the color filter group containing the infrared light filter that transmits the infrared light, and the white light image of the observed region is generated by removing the infrared component from the acquired picture signals containing the infrared components. Then, the IR picture signal corresponding to the infrared light filter is extracted from the acquired picture signals containing the infrared components, and the uniform image of the wavelength-band component (i.e., the infrared component) for which the light absorption property of the contrast region of the observed region is low is generated, based on the extracted IR picture signals. Subsequently, each picture signal of the fluorescence image of the observed region is corrected by each picture signal of the generated uniform image. Other configurations are the same as those of the first embodiment. Therefore, the same effects as those of the first embodiment can be achieved. Furthermore, the occurrence of the edge caused by the contrast region in the observed region can be more suppressed, and it is possible to easily generate the uniform image having lower contrast and reflecting the light illuminance distribution with increased accuracy. With use of each picture signal of the uniform image having the lower contrast, it is possible to correct the luminance of the fluorescence image being an observation target more accurately. As a result, it is possible to more easily obtain the fluorescence image at higher quality in which the lightness and darkness of the fluorescence caused by variation in the imaging distance to the observed region is corrected with high accuracy.

Third Embodiment

A third embodiment of the present invention will be described below. In the first and the second embodiments described above, the endoscope apparatuses 1 and 2 are described as examples of the imaging device of the present invention. However, in the third embodiment, a microscope apparatus is described as an example of the imaging device of the present invention, and descriptions of an image processing device, a computer-readable recording medium recording an image processing program, and an image processing method used by the microscope apparatus will be given subsequently.

Figure 24:
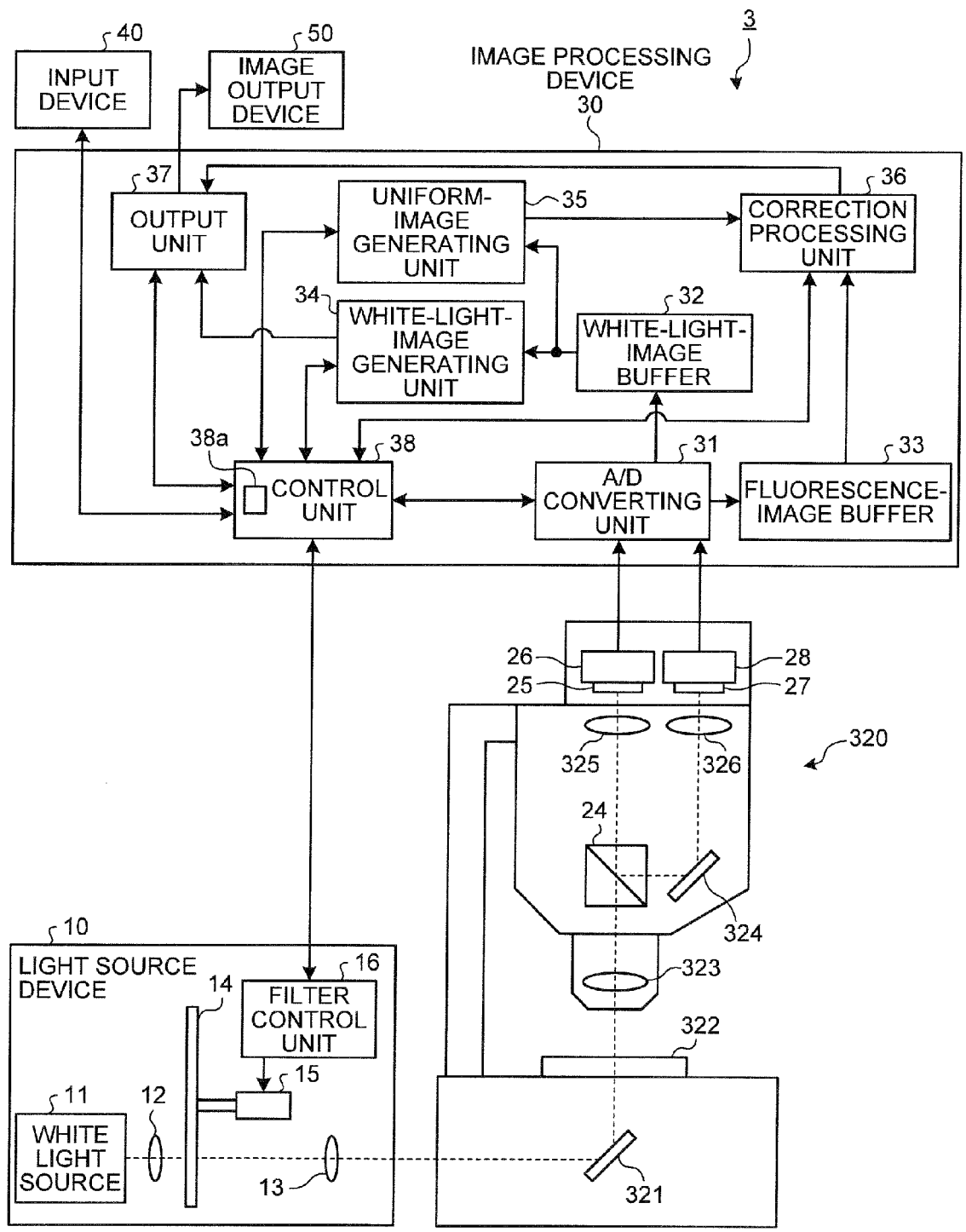
FIG. 24 is a block diagram schematically showing a configuration example of a microscope apparatus according to a third embodiment of the present invention.

FIG. 24 is a block diagram schematically showing a configuration example of the microscope apparatus according to the third embodiment of the present invention. As illustrated in FIG. 24, a microscope apparatus 3 of the third embodiment is an example of the imaging device of the present invention, and includes a microscope body 320 instead of the insertion portion 20 of the endoscope apparatus 1 of the first embodiment described above. The microscope body 320 includes the dichroic mirror 24, the color filter group 25, the white-light imaging unit 26, the barrier filter 27, and the fluorescence imaging unit 28, which are described above. The microscope body 320 also includes a reflecting mirror 321 that reflects light emitted from the light source device 10 towards a subject, an objective stage 322 on which the subject such as a body tissue is placed, an objective lens 323, a reflecting mirror 324 that reflects light from the observed region toward an optical path on the fluorescence imaging unit 28 side, a lens 325 disposed on the white-light imaging unit 26 side, and a lens 326 disposed on the fluorescence imaging unit 28 side. The other configurations of the microscope body 320 are the same as those in the first embodiment, and the same components are denoted by the same symbols.

The microscope body 320 has an imaging function for capturing a white light image and a fluorescence image of a subject to perform white light observation (color image observation) and fluorescence observation of the subject such as a body tissue. More specifically, as described above, the microscope body 320 includes the dichroic mirror 24, the color filter group 25, the white-light imaging unit 26, the barrier filter 27, the fluorescence imaging unit 28, the reflecting mirrors 321 and 324, the objective stage 322, the objective lens 323, and the lenses 325 and 326.

The reflecting mirror 321 reflects white light and excitation light alternately emitted from the light source device 10 described above toward an optical path on the objective stage 322 side (see a dashed line illustrated in FIG. 24). The objective stage 322 is provided for placing the subject such as a body tissue. The observed region of the subject placed on the objective stage 322 is alternately irradiated with the white light and the excitation light which are emitted from the light source device 10 and reflected by the reflecting mirror 321.

When an abnormal tissue, such as an affected area, in which a fluorescent agent is accumulated in advance is present in the observed region of the subject placed on the objective stage 322, the excitation light applied from the light source device 10 to the observed region via the reflecting mirror 321 passes through the observed region and excites the fluorescence agent accumulated in the abnormal tissue in the observed region. Accordingly, fluorescence in the wavelength band of 690 nm to 710 nm is generated, similarly to the first embodiment described above. On the other hand, when white light is applied from the light source device 10 to the subject on the objective stage 322 via the reflecting mirror 321, the white light from the light source device 10 passes through the observed region of the subject.

When the white light is applied from the light source device 10 to the observed region on the objective stage 322, the objective lens 323 collects normal light coming from the observed region, e.g., white light that has passed through the observed region. On the other hand, when the excitation light is applied from the light source device 10 to the observed region on the objective stage 322, the objective lens 323 collects fluorescence generated from the observed region (fluorescence generated from the fluorescent agent accumulated in the abnormal tissue in the observed region) and excitation light that has passed through the observed region.

The reflecting mirror 324 reflects the fluorescence and the excitation light, which are coming from the observed region and separated toward the optical path on the fluorescence imaging unit 28 side by the dichroic mirror 24 as described above, towards the fluorescence imaging unit 28. The lens 325 collects the white light, which is coming from the observed region and separated toward the optical path on the white-light imaging unit 26 side by the dichroic mirror 24 as described above, towards the color filter group 25. The lens 326 collects the fluorescence and the excitation light, which are coming from the observed region and reflected by the reflecting mirror 324, toward the barrier filter 27.

The microscope apparatus 3 structured as described above has an imaging function, an image processing function, and an image output function, which are identical to those of the endoscope apparatus 1 of the first embodiment described above. The microscope apparatus 3 executes the process procedure from Steps S101 to S111 illustrated in FIG. 10. Therefore, the same effects as those of the first embodiment can be achieved.

As described above, according to the third embodiment, the microscope apparatus is configured to have the imaging function, the image processing function, and the image output function identical to those of the endoscope apparatus 1 of the first embodiment. Therefore, the same effects as those of the first embodiment described above can be achieved by the microscope apparatus.

Although the white light is applied to the observed region as an example of the normal light in the first to the third embodiments described above, the present invention is not limited thereto. Any light in a wavelength band other than the excitation light may be used as the normal light applied to the observed region. Accordingly, the color component of the normal light may be set as desired.

Furthermore, although the Bayer-type color imaging element that outputs a picture signal of the single-chip imaging element is used to realize the white-light imaging unit in the first to the third embodiments described above, the present invention is not limited thereto. Any solid-state imaging elements such as a CCD or a CMOS image sensor may be used as the imaging element to realize the white-light imaging unit. For example, the imaging element may be a three-chip type solid-state imaging element that outputs a picture signal in a three-chip state or a Bayer-type solid-state imaging element.

Furthermore, although the dichroic mirror 24 is used as the dividing means for dividing light from the observed region toward the optical path on the white-light imaging unit side and the optical path on the fluorescence imaging unit side in the first and the third embodiments described above, the present invention is not limited thereto. For example, a half mirror may be used as the dividing means instead of the dichroic mirror 24 described above. In this case, it is possible to arrange, on the light receiving surface of the white-light imaging unit, an optical filter having a spectral transmittance property to remove the fluorescence and the excitation light from the observed region and transmit the white light from the observed region. Alternatively, it is possible to set the transmission wavelength band of the color filter group 25 to exclude the wavelength bands of the fluorescence and the excitation light from the observed region.

Moreover, although the half mirror 224 is used as the dividing means for dividing the light from the observed region toward the optical path on the white-light imaging unit side and the optical path on the fluorescence imaging unit side in the above-described second embodiment, the present invention is not limited thereto. For example, the dichroic mirror may be used as the dividing means instead of the half mirror 224 described above. In this case, the wavelength band of the fluorescence from the observed region may preferably be set such that it contains shorter wavelengths than those of a visible light band, and the dichroic mirror as the dividing means may preferably be configured to have the spectral characteristic that divides (transmits) the fluorescence from the observed region toward the optical path on the fluorescence imaging unit side and divides (reflects) light in a wavelength band longer than the wavelength band of the fluorescence toward the optical path on the white-light imaging unit side.

Furthermore, although the rotary filter 214 includes the white light filter 214a having the excitation-light cutting function in the second embodiment described above, the present invention is not limited thereto. For example, when a light source that is able to emit excitation light in a wavelength band shorter than that of the normal light such as the white light applied to the observed region is used, the white light filter 214a need not have the excitation-light cutting function.

Moreover, although it is determined that the wavelength band of the excitation light is 660 nm to 670 nm in the first and the third embodiments described above, the present invention is not limited thereto. The wavelength band of the excitation light may be determined as desired as long as the excitation light is able to generate fluorescence in a wavelength band other than that of the normal light (e.g., the white light) applied to the observed region.

Furthermore, in the first and the third embodiments described above, after the process of generating the white light image of the observed region (Step S102), each picture signal corresponding to the specific color filter is extracted (Step S103), and the uniform image of the wavelength-band component corresponding to the specific color filter is generated (Step S104). However, the process of generating the white light image of the observed region may be performed after any processes at Steps S103 to S109 as long as it is performed before the process at Step S110 described above.

Moreover, although the white light image of the observed region and the fluorescence image obtained by the correction process are displayed in color on the image output device 50 in the first to the third embodiments described above, the present invention is not limited thereto. For example, the image output device 50 is allowed to display the white light image of the observed region in color and display the fluorescence image of the observed region in monochrome at the same time. Furthermore, the image output device 50 described above is not limited to one that displays the white light image and the fluorescence image of the observed region on a screen. The image output device 50 may be a printer that prints out the white light image of the observed region and the fluorescence image obtained by the correction process of a printing object such as a paper, or a storage device equipped with a built-in recording medium such as a hard disk or a portable storage medium such as memory card for storing the white light image of the observed region and the fluorescence image obtained by the correction process of the recording medium.

Furthermore, although the microscope apparatus 3 having the imaging function, the image processing function, and the image output function identical to those of the first embodiment is described in the third embodiment described above, the present invention is not limited thereto. The microscope apparatus as an example of the imaging device of the present invention may be an apparatus having the imaging function, the image processing function, and the image output function identical to those of the second embodiment. In other words, the microscope apparatus of the present invention may include the light source device 210 instead of the light source device 10 of the microscope apparatus 3 of the third embodiment, the half mirror 224 instead of the dichroic mirror 24, the color filter group 225 instead of the color filter group 25, the white-light imaging unit 226 instead of the white-light imaging unit 26, the image processing device 230 instead of the image processing device 30, and, the configurations are made the same as those of the third embodiment.

Moreover, although the endoscope apparatus and the microscope apparatus for observing the subject such as a body tissue are described as an example of the imaging device of the present invention in the first to the third embodiments described above, the present invention is not limited thereto. For example, the imaging device of the present invention may be an endoscope apparatus or a microscope apparatus used in fields other than the medical field; an imaging device other than the endoscope apparatus and the microscope apparatus, such as a digital camera or a digital video camera; and a portable information terminal with an imaging function, such as a mobile phone. Moreover, the image processing device of the present invention is not limited to one installed in the medical endoscope apparatus or the medical microscope apparatus as described above. The image processing device may be installed in an endoscope apparatus or a microscope apparatus used in fields other than the medical field; an imaging device other than the endoscope apparatus and the microscope apparatus, such as a digital camera or a digital video camera; and a portable information terminal with an imaging function, such as a mobile phone.

Furthermore, in the first to the third embodiments described above, it is explained that the process procedure is executed by software by the image processing device based on operations by the control unit 38 that executes the processing program; however the present invention is not limited thereto. The image processing device of the present invention may execute the process procedure by hardware. The computer-readable recording medium in the first to the third embodiments includes an image processing program capable of performing the image processing according to the image processing method of each embodiment. The recording medium may be a built-in storage medium such as a hard disk or a portable storage medium such as a memory card.

According to the image processing device, the imaging device, the computer program product having the computer-readable recording medium including the image processing program, and the image processing method according to the first to the third embodiments described above, luminance of the fluorescence image of the observation target can be corrected accurately with a simple structure.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing device comprising:
a normal-light-image storage unit that stores therein each picture signal of a normal light image of an observed region, the normal light image being captured by a normal-light imaging unit that receives normal light from the observed region via a plurality of color filters having different spectral characteristics;
a fluorescence-image storage unit that stores therein each picture signal of a fluorescence image of the observed region, the fluorescence image being captured by a fluorescence imaging unit that receives fluorescence generated from the observed region irradiated with excitation light;
a uniform-image generating unit that extracts each picture signal corresponding to a specific color filter, which is one of the plurality of color filters and transmits light in a wavelength band for which a light absorption property of a contrast region in the observed region is low, from among each picture signal of the normal light image stored in the normal-light-image storage unit, and generates a uniform image of a wavelength-band component corresponding to the specific color filter based on each extracted picture signal; and
a correction processing unit that corrects each picture signal of the fluorescence image stored in the fluorescence-image storage unit by using the uniform image;
wherein the plurality of color filters include a plurality of red light filters that transmit red light, a plurality of green filters that transmit green light, and a plurality of blue filters that transmit blue light, and
the red light filters among the plurality of color filters serve as the specific color filter; and
wherein:
the uniform-image generating unit includes:
a signal extracting unit that extracts each picture signal corresponding to the red light filter from among each picture signal of the normal light image stored in the normal-light-image storage unit; and
an interpolation processing unit that performs an interpolation process of each picture signal extracted by the signal extracting unit to generate the uniform image of a wavelength-band component corresponding to the red light filter.

2. The image processing device according to claim 1, wherein
the plurality of color filters include a plurality of red light filters that transmit red light, a plurality of green light filters that transmit green light, a plurality of blue light filters that transmit blue light, and a plurality of infrared light filters that transmit infrared light, and
the infrared light filters in the plurality of color filters serve as the specific color filter.

3. The image processing device according to claim 2, wherein
the uniform-image generating unit includes
a signal extracting unit that extracts each picture signal corresponding to the infrared light filter from among each picture signal of the normal light image stored in the normal-light-image storage unit; and
an interpolation processing unit that performs an interpolation process of each picture signal extracted by the signal extracting unit to generate the uniform image of a wavelength-band component corresponding to the infrared light filter.

4. The image processing device according to claim 1, wherein the correction processing unit includes
a standardization processing unit that performs a standardization process on luminance of the fluorescence image by dividing a picture signal of the fluorescence image by a picture signal of the uniform image for each corresponding pixel between the uniform image and the fluorescence image.

5. The image processing device according to claim 1, wherein
the correction processing unit includes
an offset processing unit that performs an offset process of uniformly adding a predetermined value to each picture signal of the uniform image, and
the correction processing unit corrects each picture signal of the fluorescence image by using the uniform image subjected to the offset process.

6. The image processing device according to claim 1, wherein
the correction processing unit includes
a clipping processing unit that performs a clipping process of comparing a signal value of each picture signal of the uniform image with a predetermined reference value of the picture signal and replacing a signal value larger than the reference value with the reference value, and
the correction processing unit corrects each picture signal of the fluorescence image by using the uniform image subjected to the clipping process.

7. An imaging device comprising:
a light source unit that switchably applies normal light and excitation light to an observed region;
a normal-light imaging unit that includes a plurality of color filters having different spectral characteristics and captures a normal light image of the observed region by receiving, via the plurality of color filters, normal light from the observed region irradiated with the normal light;
a fluorescence imaging unit that captures a fluorescence image of the observed region by receiving fluorescence generated from the observed region irradiated with the excitation light;
a uniform-image generating unit that extracts each picture signal corresponding to a specific color filter, which is one of the plurality of color filters and transmits light in a wavelength band for which a light absorption property of a contrast region in the observed region is low, from among each picture signal of the normal light image captured by the normal-light imaging unit, and generates a uniform image of a wavelength-band component corresponding to the specific color filter based on each extracted picture signal; and
a correction processing unit that corrects each picture signal of the fluorescence image captured by the fluorescence imaging unit by using the uniform image;
wherein the plurality of color filters include a plurality of red light filters that transmit red light, a plurality of green filters that transmit green light, and a plurality of blue filters that transmit blue light, and the red light filters among the plurality of color filters serve as the specific color filter; and wherein:

the uniform-image generating unit includes:

a signal extracting unit that extracts each picture signal corresponding to the red light filter from among each picture signal of the normal light image stored in the normal-light-image storage unit; and an interpolation processing unit that performs an interpolation process of each picture signal extracted by the signal extracting unit to generate the uniform image of a wavelength-band component corresponding to the red light filter.

8. A computer readable device recording programmed instructions for performing an image processing, wherein the instructions, when executed by a computer, cause the computer to perform:

acquiring each picture signal of a normal light image of an observed region, the normal light image being captured by a normal-light imaging unit that receives normal light from the observed region via a plurality of color filters having different spectral characteristics, and each picture signal of a fluorescence image of the observed region, the fluorescence image being captured by a fluoresce imaging unit that receives fluorescence generated from the observed region irradiated with excitation light;

extracting each picture signal corresponding to a specific color filter, which is one of the plurality of color filters and transmits light in a wavelength band for which a light absorption property of a contrast region in the observed region is low;

generating a uniform image of a wavelength-band component corresponding to the specific color filter based on each picture signal extracted at the extracting; and correcting each picture signal of the fluorescence image by using the uniform image;

wherein the plurality of color filters include a plurality of red light filters that transmit red light, a plurality of green filters that transmit green light, and a plurality of blue filters that transmit blue light, and the red light filters among the plurality of color filters serve as the specific color filter; and wherein the extracting comprises extracting each picture signal corresponding to the red light filter from among each picture signal of the normal light image; and wherein the instructions, when executed by the computer, further cause the computer to perform an interpolation process that performs an interpolation of each picture signal extracted by the signal extracting process to generate the uniform image of a wavelength-band component corresponding to the red light filter.

9. An image processing method comprising:

acquiring each picture signal of a normal light image of an observed region, the normal light image being captured by a normal-light imaging unit that receives normal light from the observed region via a plurality of color filters having different spectral characteristics, and each picture signal of a fluorescence image of the observed region, the fluorescence image being captured by a fluoresce imaging unit that receives fluorescence generated from the observed region irradiated with excitation light;

extracting each picture signal corresponding to a specific color filter, which is one of the plurality of color filters and transmits light in a wavelength band for which a light absorption property of a contrast region in the observed region is low;

generating a uniform image of a wavelength-band component corresponding to the specific color filter based on each picture signal extracted at the extracting; and correcting each picture signal of the fluorescence image by using the uniform image;

wherein the plurality of color filters include a plurality of red light filters that transmit red light, a plurality of green filters that transmit green light, and a plurality of blue filters that transmit blue light, and the red light filters among the plurality of color filters serve as the specific color filter; and wherein the extracting comprises extracting each picture signal corresponding to the red light filter from among each picture signal of the normal light image; and wherein the method further comprises an interpolation process that performs an interpolation of each picture signal extracted by the signal extracting process to generate the uniform image of a wavelength-band component corresponding to the red light filter.

* * * * *